US005684587A

United States Patent [19]

Naqwi

[11] Patent Number: 5,684,587

[45] Date of Patent: Nov. 4, 1997

[54] DEVICE AND PROCESS FOR INTERFEROMETRIC SIZING OF PARTICLES USING SPATIAL FILTERING OF SCATTERED RADIATION

[75] Inventor: Amir A. Naqwi, Shoreview, Minn.

[73] Assignee: TSI Incorporated, St. Paul, Minn.

[21] Appl. No.: 677,381

[22] Filed: Jul. 5, 1996

[51] Int. Cl.$^6$ .................................................. G01B 9/02

[52] U.S. Cl. ......................... 356/345; 356/357; 356/336

[58] Field of Search ................................. 356/336, 345, 356/357, 359, 360

[56] References Cited

U.S. PATENT DOCUMENTS

| | | |
|---|---|---|
| 3,915,572 | 10/1975 | Orloff . |
| 3,953,128 | 4/1976 | Holly . |
| 4,948,257 | 8/1990 | Kaufman . |
| 4,986,659 | 1/1991 | Bachalo . |
| 5,432,605 | 7/1995 | Naqwi . |
| 5,453,837 | 9/1995 | Naqwi . |
| 5,513,004 | 4/1996 | Naqwi . |

FOREIGN PATENT DOCUMENTS

| | | |
|---|---|---|
| 2448651 | 4/1975 | Germany . |

OTHER PUBLICATIONS

Intl. Appln. No. WO 95/03524, Amir A. Naqwi, "Interferometric Cylinder Sizing and Velocimetry Device".

*Primary Examiner*—Frank G. Font

*Assistant Examiner*—Robert Kim

*Attorney, Agent, or Firm*—Frederick W. Niebuhr; Haugen and Nikolai, P.A.

[57] ABSTRACT

An apparatus for non-contact measurement of particles, fibers and other light scattering elements includes two laser beams that intersect one another to form a measuring region within a composite flow. Particles in the flow scatter the laser energy as they traverse the measuring region. Scattered energy is received by a pair of optical detectors that generate respective electrical signals based on received energy. The detectors have selectively contoured non-rectangular apertures to controllably vary transmittance and as a result generate phase differences according to a corresponding non-linear function that relates the phase differences to particle diameters. One particularly effective aperture shape includes opposite sides contoured according to a lognormal function, to resemble an onion or tear drop. Triangular and trapezoidal apertures also can be used to achieve non-linear functions. In alternative embodiments, rectangular apertures are used in combination with energy attenuation filters with selective gradients in thickness or transmissivity. The result is a selected variance of transmittance in the detector similar to that achieved by controlling the aperture shape.

27 Claims, 13 Drawing Sheets

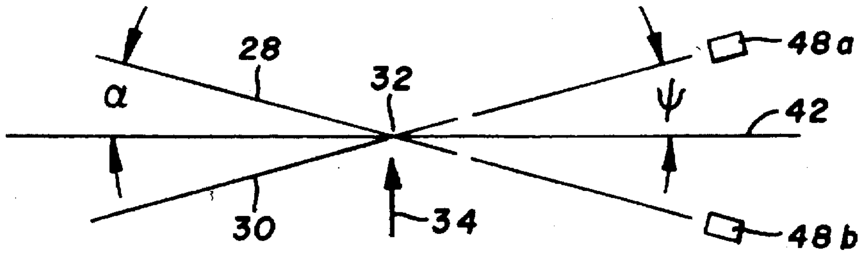
FIG.3
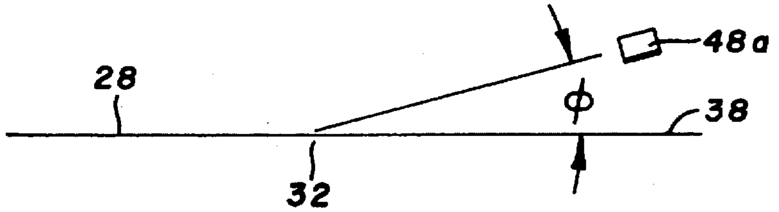
FIG.4
FIG.5
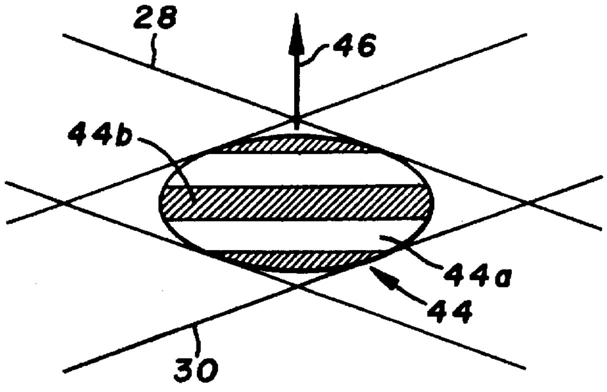
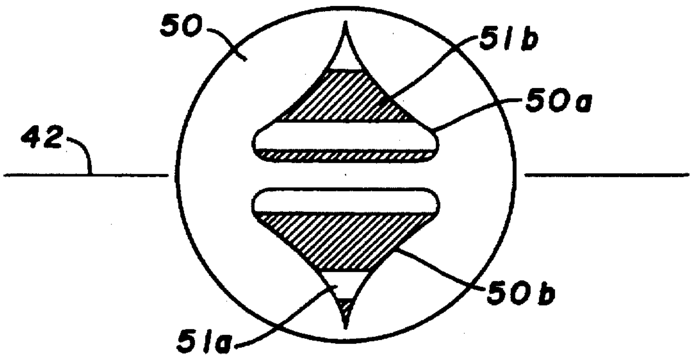
FIG.6

DEVICE AND PROCESS FOR INTERFEROMETRIC SIZING OF PARTICLES USING SPATIAL FILTERING OF SCATTERED RADIATION

BACKGROUND OF THE INVENTION

The present invention relates to instrumentation for non-contact measurement to determine size, velocity and other characteristics of objects such as air-borne and liquid-borne particles, spherical elements or elongated elements including fibers. For convenience, these objects are referred to as particles light scattering elements.

The instrumentation is used to examine multiphase or composite flows such as liquid sprays, where moving droplets represent the particulate medium and the surrounding air is the continuous medium. It is of interest to take localized non-contact measurements of drop size and velocity in a spray. Phase Doppler measurement techniques have been used successfully to obtain such measurements.

Phase Doppler devices employ an optical interferometric technique that is an extension of laser Doppler velocimetry (LDV), in which light scattered by individual particles is collected and analyzed. The oscillation frequency of LDV signals represents the velocity of the light scattering particles. In a phase Doppler system, at least two receivers collect scattered radiation from different regions of space, and two oscillating signals are measured. The phase shift between these signals indicates particle size.

The phase Doppler technique also may be used in a manufacturing environment to monitor quality of the products such as spray nozzles. It may be employed to control a manufacturing process, such as fiber drawing, to continuously measure the diameter of the fiber to ensure uniformity.

Conventionally in the phase Doppler technique, signal receivers are represented by point detectors, i.e. receiving apertures with infinitesimally small dimensions. While real receivers have finite-area openings, idealization of the point detector assumes that the phase response of a finite receiving aperture can be represented accurately by a point detector. In other words, the phase centroid of a finite aperture, i.e. the location of a theoretical point detector with the same phase response as the finite-area detector, is assumed to be fixed. Thus, the functional relationship between the phase shift and the particle size was not thought to be affected by any difference between a real receiver with a finite area aperture and an ideal point receiver with an infinitesimally small area aperture.

The most common functional relationship between the phase shift and the particle size for a point detector is a linear one, with the phase shift expressed as a constant multiplied by the particle size. This relationship has been assumed for a finite-area aperture as well, so that the finite aperture is represented by an equivalent point detector.

Research leading to the present invention, however, shows that phase centroids of real apertures are fixed only for certain aperture shapes and certain particle size ranges. Thus far, designers and developers of the phase Doppler systems have unintentionally selected aperture shapes and particle size ranges that entail nearly fixed phase centroids. The phenomenon of displacement of the phase centroid with increasing particle size has not been recognized, nor has it been used to advantage in the design of phase Doppler systems.

Systems designed according to the assumed linear relationship are subject to several shortcomings. The first is a limited range over which phase differences can unambiguously measure particle sizes. An initial 2π cycle (0°–360°) corresponds to a nominal range of particles up to a nominal size or diameter. Of course, systems can be configured so that the initial 2π cycle encompasses a broader range of particle sizes, but system sensitivity (phase shift per incremental diameter change, e.g. degrees/micron) is reduced. One known approach to overcoming this limitation involves using three detectors to obtain two different sets of phase difference values: one set affording higher sensitivity, and the other affording a wider range of particle sizes. This approach adds considerably to the expense of the system, because it requires an additional energy detector and the associated electronics for generating an electrical signal based on received energy.

Another feature of linear systems is a lack of uniformity in signal intensity. As the size of measured particles increases, the signal strength also increases, generally in proportion to the square of the particle diameter. This can lead to error, because the greater signal strength increases the detection of signals due to particles that cross the periphery of the measuring volume where illumination is substantially less uniform. The lack of uniform intensity affects analog components of the detector, and reduces the uniformity of bit-resolution in analog-to-digital conversions. Accordingly, it would be advantageous to counteract the tendency of increasing signal strength with increasing diameter.

Therefore, it is an object of the present invention to provide an interferometric measuring system, in which the scattered coherent energy is selectively filtered to obtain a desired non-linear functional relationship between phase differences and particle sizes over a desired size range.

Another object is to provide an apparatus for non-contact measurement of light scattering elements in which a 2π cycle of phase differences encompasses a wider range of particle diameters as compared to a size range attainable according to the conventional linear phase/diameter relationship.

A further object is to provide a process for measuring light scattering elements that employs spatial filtering to prevent phase shift values from exceeding 360° over a large range of particle sizes, to avoid the ambiguity in conventional systems when detected phase shifts exceed 360°.

Yet another object is to provide an interferometric particle measuring system in which signal visibility decreases as the particle diameters increase, counteracting non-uniformity due to increases in signal strength with increasing diameters.

SUMMARY OF THE INVENTION

To achieve the above and other objects, there is provided an apparatus for non-contact measurement of light scattering elements. The apparatus includes a beam generating means for generating two linearly propagating beams of coherent energy. The beams are oriented at a predetermined beam angle relative to one another, and intersect one another to define a beam plane. The beams interfere with one another over a measuring region to form interference fringes extending across the measuring region in parallel fashion. An alignment means, operatively associated with the beam generating means, positions the beams with respect to a composite flow so that light scattering elements within the composite flow move through the measuring region.

An energy detecting means senses the coherent energy scattered by each of the light scattering elements as it traverses the beam intersection zone. The detecting means includes first and second detectors having first and second apertures at respective first and second locations spaced apart from the beam intersection zone. The energy detecting means generates respective first and second detector signals responsive to the energy received through the first and second apertures, respectively. The coherent energy received at each of the apertures includes a projection of the interference fringes traveling across the aperture in a fringe movement direction normal to a lengthwise extension of the projected fringes. A data generating means generates scattering element size information in response to receiving the first and second detector signals. The data generating means includes a signal processing means for generating phase difference values representing temporal shifts between the first and second detector signals. A conversion means generates the scattering element size information based on the phase difference values.

At least one of the apertures includes a coherent energy filtration means for determining a transmittance pattern in which transmittance of the aperture is controllably varied in the fringe movement direction. Consequently the phase difference values, when generated responsive to light scattering elements having sizes within a predetermined size range, are generated according to a non-linear function over at least a part of a selected $2\pi$ cycle of the phase difference values corresponding to the selected size range. The conversion means generates the scattering element size information substantially according to the non-linear function.

In accordance with the present invention, selecting a transmittance pattern to achieve the desired non-linearity, also called selective spatial filtration, results in significant displacement of the phase centroid with increasing particle size. Such displacement can considerably extend the size range of a system while maintaining a high sensitivity for measuring particles at the lower end of the measuring range. More particularly, the energy receiving apertures can be masked to provide specially shaped non-rectangular profiles, in which the aperture width varies in the direction of aperture height, i.e. the fringe movement direction. The function relating phase difference to particle size (e.g. degrees/micron) exhibits a slope that in general decreases with increasing particle size. The steeper slope represents higher sensitivity where it is needed most, at the smaller diameter end of the size range. The more gradual slope, corresponding to the large diameter segment of the size range, represents an extension of the measuring range to encompass larger particles measurable within a given $2\pi$ cycle of phase differences.

The desired result can be achieved by a variety of non-

When the apertures are near the symmetry plane, e.g. where the elevation angle is less than about five degrees, the particle size range of interest corresponds to the initial $2\pi$ cycle of phase differences. For measuring larger particles, the apertures can be positioned relatively remote from the symmetry plane (i.e. with larger elevation angles), in which case the particle size range corresponds to another phase cycle, e.g. 361°–720°, 721°–1080°, etc.

The present invention can be practiced in traditional phase Doppler systems in which the detector apertures are spaced apart from the beam plane (non-zero off-axis angle), or in planar systems in which the apertures are within the beam plane. In either event, pairs of apertures with appropriately selected transmittance patterns provide a favorable combination of measurement sensitivity for smaller diameter light scattering elements, and substantial expansion of a "large particle" segment of a given particle size range. A much larger domain of particle sizes can be measured without introducing the $2\pi$ ambiguity when a portion of the size range extends into the next cycle of phase differences. Accordingly, there is no need to counteract such ambiguity with a third detector and accompanying electronics. Another favorable feature is the reduction in signal visibility with increasing particle size, which counteracts the increasing signal strength to provide more uniform optical signals over a given range of particle sizes.

Thus according to the present invention, energy receiving apertures in interferometric measuring systems are selectively configured as to their transmittance, to derive the above advantages from a non-linear relationship of phase differences versus particle diameters, a phenomenon previously unrecognized; or to the extent recognized, avoided. By selective spatial filtration of the scattered light, a significant displacement of the phase centroid with increasing particle size is achieved. This effect can be used to extend the size range of a system while maintaining a high sensitivity to measure small particles.

IN THE DRAWINGS

For a further understanding of the invention and its features, reference is made to the detailed description and to the drawings, in which:

FIGS. 3 and 4 are schematic illustrations of system

DETAILED DESCRIPTION OF THE PREFERRED EMBODIMENT

Figure 1:
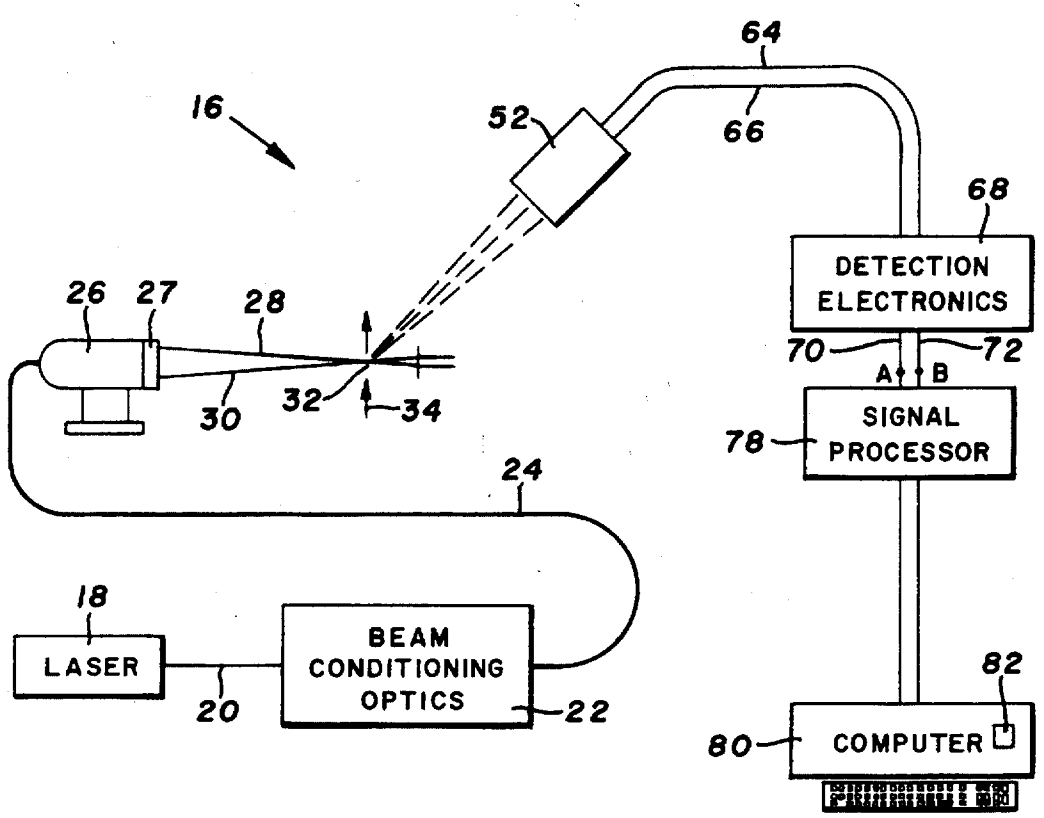
FIG. 1 is schematic view of an interferometric particle measuring system constructed in accordance with the present invention.

Turning now to drawings, there is shown in FIG. 1 an interferometric system 16 for sizing particles, droplets and other light scattering elements. The system includes a laser head 18 with a diode laser and beam collimating optics (not shown) for generating a laser beam 20. The laser beam is received by beam conditioning optics 22 including a beam splitter, to produce a pair of collimated laser beams. While system 16 utilizes a single pair of monochromatic beams for measuring velocities (and velocity vector components) in one direction, color separating prisms can be used to produce several pairs of beams distinguishable by color, for obtaining velocity information in two or three dimensions.

Optical fibers in a cable 24 carry the laser energy to a transmitting device 26, where the fiber optic cable output is directed through focusing lens 27 to produce two laser beams 28 and 30. Emerging from the transmitting device, beams 28 and 30 are oriented at an angle of 2α and caused to intersect at a measuring region 32, i.e. the volume over which the two beams intersect. The beams also are focused at the measuring region. Throughout the measuring region, beams 28 and 30 interfere with one another to form interference fringes.

Transmitting device 26 is manipulated to position the measuring region with a two-phase flow 34 that includes particles or other light scattering elements and a medium in which the particles are supported. For example, the flow can consist of solid particles in an air or gas stream, liquid droplets in a gaseous medium, solid particles in a liquid stream, or gaseous elements (bubbles) in a liquid.

The geometry of measurement system 16 is illustrated in FIGS. 3 and 4. FIG. 3 illustrates laser beams 28 and 30 propagated in a beam plane 38 coincident with the plane of FIG. 3 and appearing as a line in FIG. 4. Each beam is separated from a beam axis 40 that bisects the angle 2α between beams 28 and 30, i.e. is disposed at an angle α relative to each beam. Beam axis 40 also is the intersection of beam plane 38 and a plane of symmetry 42 perpendicular to the beam plane. Symmetry plane 42 appears as a line in FIG. 3 and coincides with the plane of FIG. 4.

As seen in FIG. 5, measuring region 32 is a substantially ellipsoidal volume defined by the intersection of laser beams 28 and 30. The beam angle α is exaggerated in this figure, to more clearly show a series of interference fringes 44, including alternating right fringes 44*a* and dark fringes 44*b* formed throughout the measuring region and parallel to symmetry plane 42. As a particle moves through the measuring volume, the scattered coherent energy fluctuates according to the light and dark fringes in a cyclical pattern that provides a velocity vector 46 perpendicular to the plane of symmetry. If flow 34 moves parallel to vector 46 as indicated by the arrow in FIGS. 1 and 3, then vector 46 represents the full particle velocity. Otherwise, the vector represents a component of the velocity in the vertical direction in FIGS. 1, 3 and 5. The light scattered by the particles is collected at two detecting locations, represented schematically in FIG. 3 as separate detectors 48*a* and 48*b* on opposite sides of symmetry plane 42, and symmetrical in the sense that the respective linear paths traversed by scattered energy from measuring region 32 to the detectors defines the same elevation angle Ψ from the plane of symmetry. Detectors 48*a* and 48*b* are close to symmetry plane 42 with the elevation angle being at most about 3°. As a result, a non-linearity in phase difference relative to particle sizes, discussed below, occurs during the initial 2π cycle, i.e. 0°–360° as opposed to subsequent cycles of up to 720°, 1080°, etc.

Also, as seen in FIG. 4, the detector positions 48*a* and 48*b* are spaced apart from beam plane 38 by a distance in both cases determined by an off-axis angle Φ.

In actual practice, detectors 48*a* and 48*b* are part of a single optical receiving device 52 with a single, circular receiving lens 54 covered by a mask 50, as best seen in FIG. 6. Two openings are formed through the mask, symmetrical in the vertical direction about the mask center. When the mask and receiving lens are centered on symmetry plane 42, the openings provide energy receiving apertures 50*a* and 50*b*, spaced apart and symmetrically arranged about the plane of symmetry.

As each particle traverses measuring region 32, it encounters the alternating interference fringes 44*a* and 44*b* and scatters light in a corresponding alternating sequence. The result is a projection of scattered light onto apertures 50*a* and 50*b* that includes alternating bright and dark projected fringes 51*a* and 51*b*. Particle movement causes projected fringes 51 to move across the apertures in a fringe movement direction. With apertures 50*a* and 50*b* positioned above and below symmetry plane 42 as described, the fringe movement direction as viewed in FIG. 6 is vertically upward.

Figure 7:
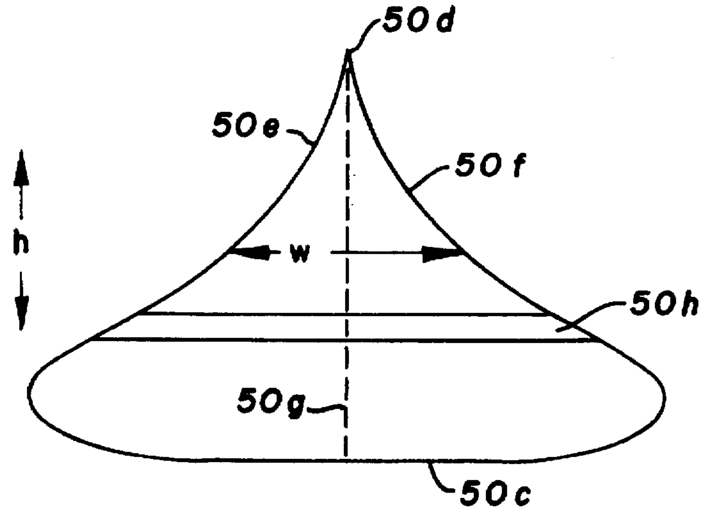

Apertures 50*a* and 50*b* are selectively shaped to vary their transmittance of the scattered coherent energy according to a particular transmittance pattern. With reference to FIG. 7, aperture 50*a* includes a lower end 50*c* of minimum height, an upper end 50*d* of maximum height that more closely resembles a point. The height (50*d*–50*c*) is at least about 75% of the projected fringe spacing, i.e. the combined width of a bright fringe and adjacent dark fringe. More preferably, the height exceeds the fringe spacing but is less than about 20 times the fringe spacing. Two opposite side walls 50*e* and 50*f* symmetrical about a vertical center line 50*g*, to yield a shape that resembles an onion or teardrop. In the direction of increasing height, a width w, horizontal in FIG. 7, at first increases to a maximum then diminishes as the height increases toward maximum 50*d*. More particularly, side walls 50*e* and 50*f* are contoured to vary the aperture width according to a lognormal function selected to vary transmittance through a band 50*h* of a given thickness, as the band is moved vertically across the aperture. Because the tranmissivity of a receiving lens 54 is uniform, the transmittance pattern through the aperture is governed entirely by the variance in aperture width. Side walls 50*e* and 50*f* cooperate to vary the aperture width according to a lognormal function selected to achieve a desired non-linear relationship of phase differences to particle sizes. The basis for the function, leading to the chosen contour, is explained in the Appendix below.

It is to be appreciated that aperture 50*b* has the same shape, but is inverted to provide symmetry about a horizontal center line of mask 50.

rectangular shapes, including trapezoidal and triangular apertures. A particularly advantageous profile has opposite side walls contoured according to a logonormal function, with the aperture as a whole resembling an onion or tear drop in shape. A pair of apertures having this shape are advantageously arranged on opposite sides of a plane of symmetry orthogonal to the beam plane and bisecting the beam angle. The aperture pair also should be symmetrical about the symmetry plane. This arrangement has been found to extend the size range by a factor of three as compared to a "nominal" size range following the conventional linear relationship of phase and diameter.

Although selecting the aperture shape is the preferred approach to achieving a selected transmittance pattern, an energy attenuation device can be used in combination with a conventional rectangular aperture. The device can be a substantially transparent plate with a selectively varied thickness in the fringe movement direction, or a uniform thickness in combination with a controllably varied transmissivity.

zontal axis represents time and the vertical axis represents voltage or power of received scattered energy. Signals 74 and 76 have the same frequency but are shifted in phase. The difference in phase is represented by the horizontal displacement of signal 76 relative to signal 74. For more detailed information regarding the detection electronics, reference is made to U.S. Pat. No. 5,432,605, assigned to the assignee of this application.

Figure 9:
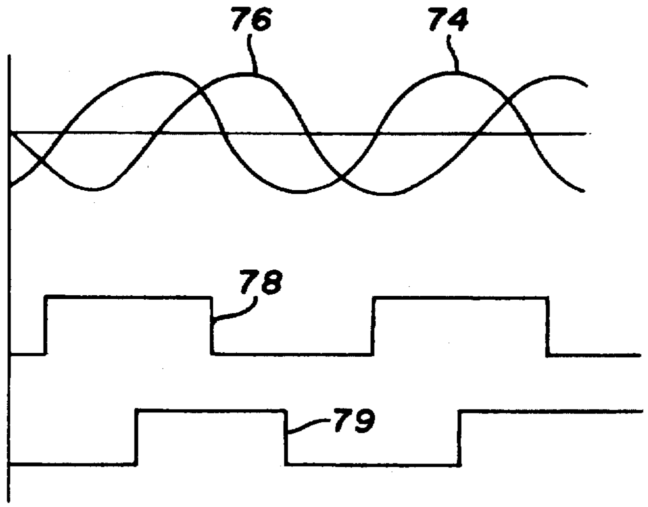

The respective analog electrical signals are provided to a signal processor 78, which converts them to digital information and processes the information to determine the signal frequency, phase shift, the residence time of a particle within measuring region 32, and the interval between the current pair of signals and the pair of signals corresponding to the previous particle's traverse of the measuring region. FIG. 9 illustrates the corresponding digital signals at 78 and 79, with zero crossings of the analog signal triggering digital signal transitions.

The processor information, particularly frequency and phase shift, is transferred to a computer 80, where signal frequencies are converted into particle velocities, and phase differences are converted into particle sizes. More specifically, the computer includes a phase/diameter processor 82, configured either as a look-up table to generate specific diameter outputs based on specific phase difference inputs, or as a function generator to calculate diameters based on phase differences according to a predetermined function. The look-up table approach is preferred in this instance, and in general.

Figure 10:
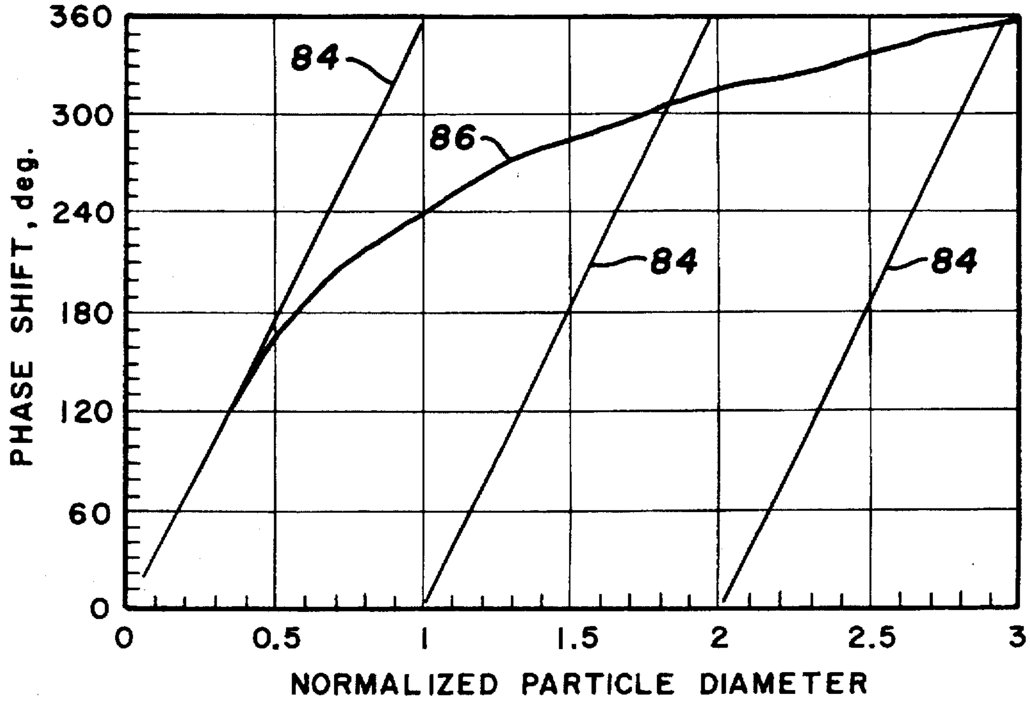

Processors of the same type as processor 82 are known, and have been used in connection with generating particle size information based on phase differences. However, conventional processors have been configured based on the assumption of a linear relationship between measured phase differences and particle sizes. The conventionally assumed linear relationship is illustrated in FIG. 10 by a straight line 84 with a constant slope normalized to 360° per diameter "unit". Particles with diameters larger than one unit lead to actual phase differences of greater than 360°. Because measured phase differences cannot exceed 360°, such larger particles create "2π" ambiguities which can be resolved using three energy detectors to provide a pair of phase difference readings for each particle, e.g. as explained in U.S. Pat. No. 5,513,004 assigned to the assignee of this application.

In accordance with the present invention, however, the 2π

Figure 8:
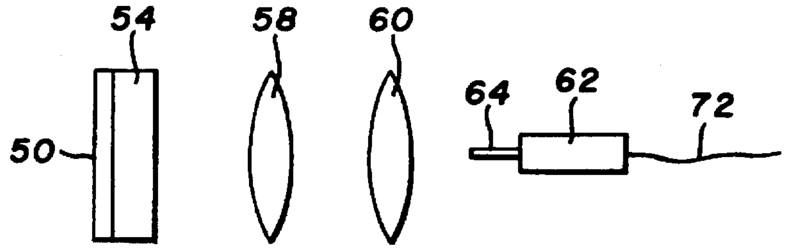
Figure 11:
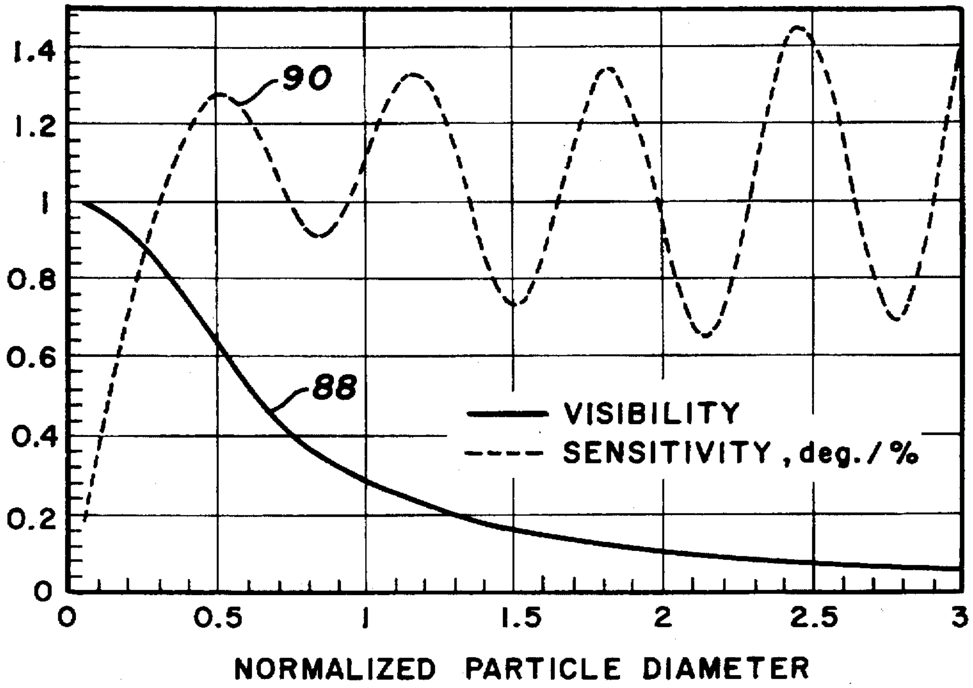

FIGS. 3 and 4 are schematic illustrations of system components illustrating the geometry of the system;

FIG. 5 is an enlarged view of a beam intersection zone or measuring region of the system;

FIG. 6 shows a pair of detector apertures of the system, that receive scattered coherent energy;

FIG. 7 is an enlarged view of one of the apertures;

FIG. 8 is a schematic view of optical components associated with one of the apertures;

FIG. 9 is a timing diagram showing analog and digital electrical signals generated as a result of scattered light received through the aperture;

FIG. 10 is a graph of phase shift as a function of normalized particalized diameter, with curves representing a conventional system having a linear phase/diameter relationship and a non-linear phase/diameter function corresponding to the pair of contoured apertures shown in FIG. 6;

FIG. 11 is a chart illustrating signal visibility and sensitivity as functions of normalized particle diameter, when using the contoured apertures of FIG. 6;

traverse the apertures. The base or pedestal level represents a minimum intensity level associated with a predominance of dark fringes projected onto the aperture. Clearly the visibility decreases with increasing particle size, throughout the range but particularly along a segment of about 0.3–0.8 times the nominal diameter. This reduction in signal visibility is advantageous, because it counteracts the increase of signal intensity with the square of the particle diameter. Thus, excessive amplitude fluctuations at larger diameters are diminished, and signal strength is more uniform over a wider range of particle sizes. As a result, analog components are less susceptible to unwanted fluctuations, and analog component outputs are more suitable for uniform bit-resolution in analog-to-digital conversion. The diminishing visibility counteracts another unwanted feature; namely, the tendency to detect signals from peripheral portions of the measuring volume as particle sizes increase. Such peripheral measurements are more prone to error, because the interference fringes are less uniform. The reduction in signal visibility decreases this source of error.

As seen from curve 90, sensitivity (degrees of phase difference/percent variation in particle size), fluctuates over the size range beginning at about 0.3 times the nominal diameter. Fluctuation is generally about a value of 1° in phase shift for a 1% shift in diameter.

Figure 12:
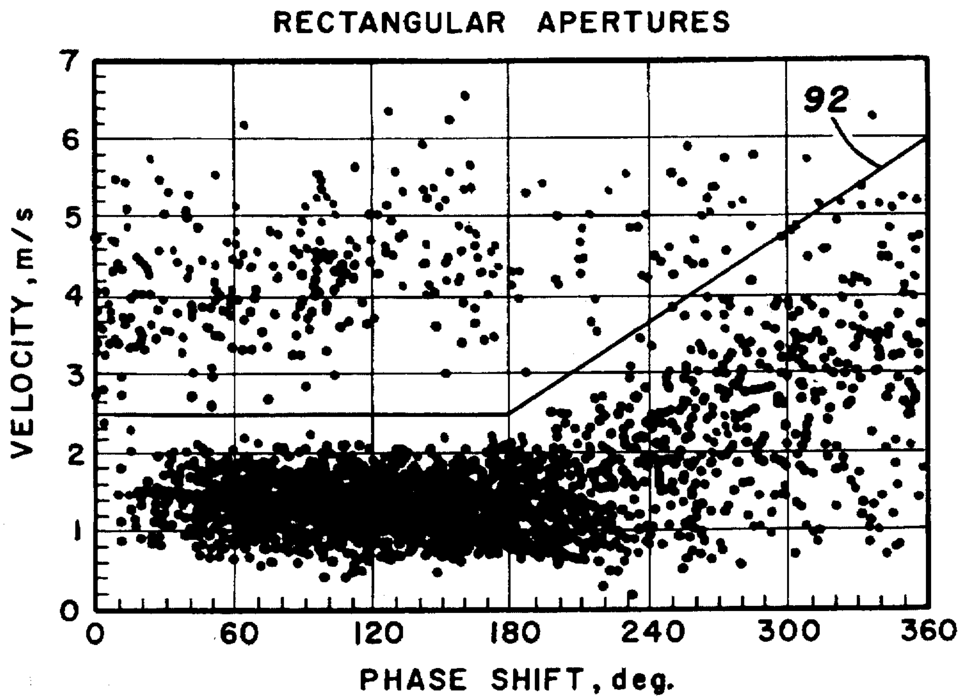
FIG. 12 illustrates phase shifts and velocities of multiple individual droplets in a spray, with measurements taken using rectangular apertures having the same geometrical centroids as the contoured apertures shown in FIG. 6.
Figure 13:
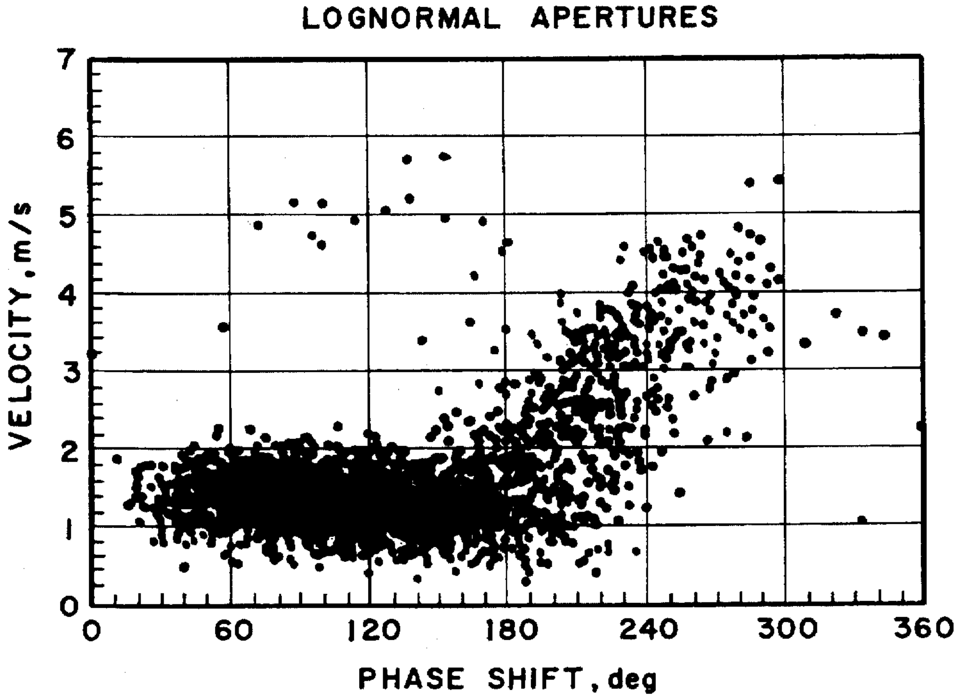
FIG. 13 illustrates multiple measurements of droplet velocity versus phase shift, with measurements taken using the contoured apertures illustrated in FIG. 6.

Experimental results confirm the non-linear functional relationship by curve 86 shown in FIG. 10. FIGS. 12 and 13 illustrate individual phase difference measurements and related velocities. Measurements were taken of a spray of water, in which droplet velocity correlates strongly with droplet size in that larger droplets move faster. Measurements were taken with an Adaptive Phase/Doppler Velocimeter (available from TSI Incorporated). The energy detecting apertures were selectively masked to provide narrow rectangular apertures for the measurements shown in FIG. 12, and contoured lognormal apertures for taking the measurements shown in FIG. 13. In both cases, the apertures were proximate the plane of symmetry, and symmetrically arranged on opposite sides of that plane. The narrow rectangular apertures and the lognormal apertures had the same geometric centroids.

FIG. 12 shows phase differences exceeding 360° in the case of rectangular apertures. These episodes of higher phase difference are shown as data points above a dividing line 92. The actual phase difference for such points is the value indicated in the figure, plus 360°.

Figure 14:
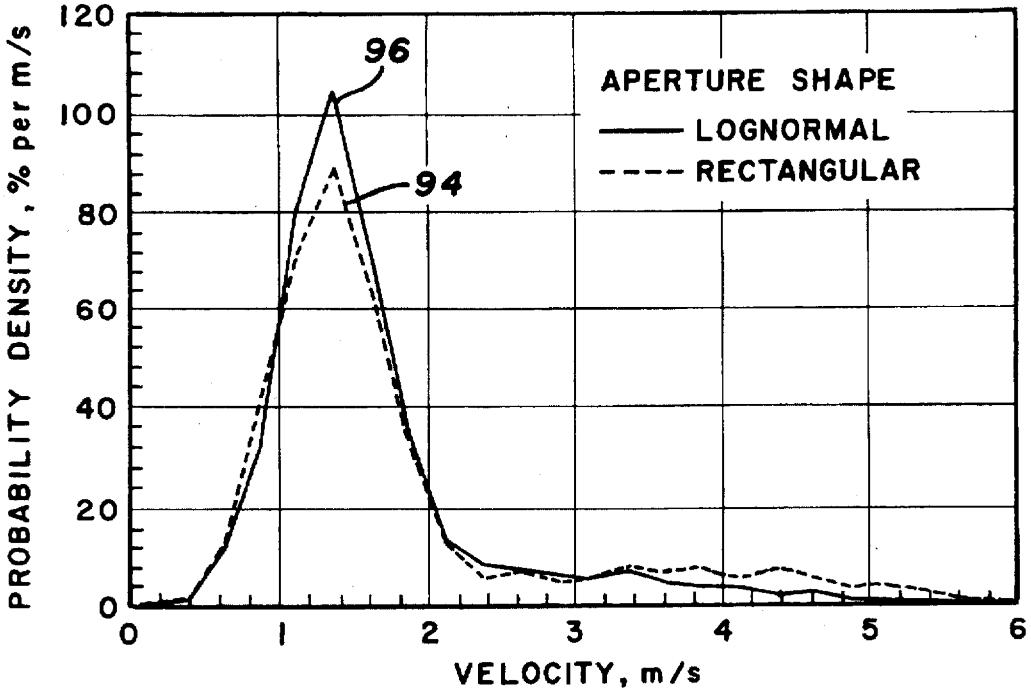
FIG. 14 is a chart showing a measured probability density of droplet velocity, comparing measurements taken with the contoured apertures shown in FIG. 6 and with rectangular apertures.

The measured velocity distributions are compared in FIG. 14, with the rectangular aperture distribution and lognormal aperture distribution indicated at 94 and 96, respectively. The rectangular apertures measure a greater proportion of high speed signals corresponding to larger droplets. This shows the higher visibility of the larger droplets to the narrow rectangular apertures as compared to the lognormal apertures.

Figure 15:
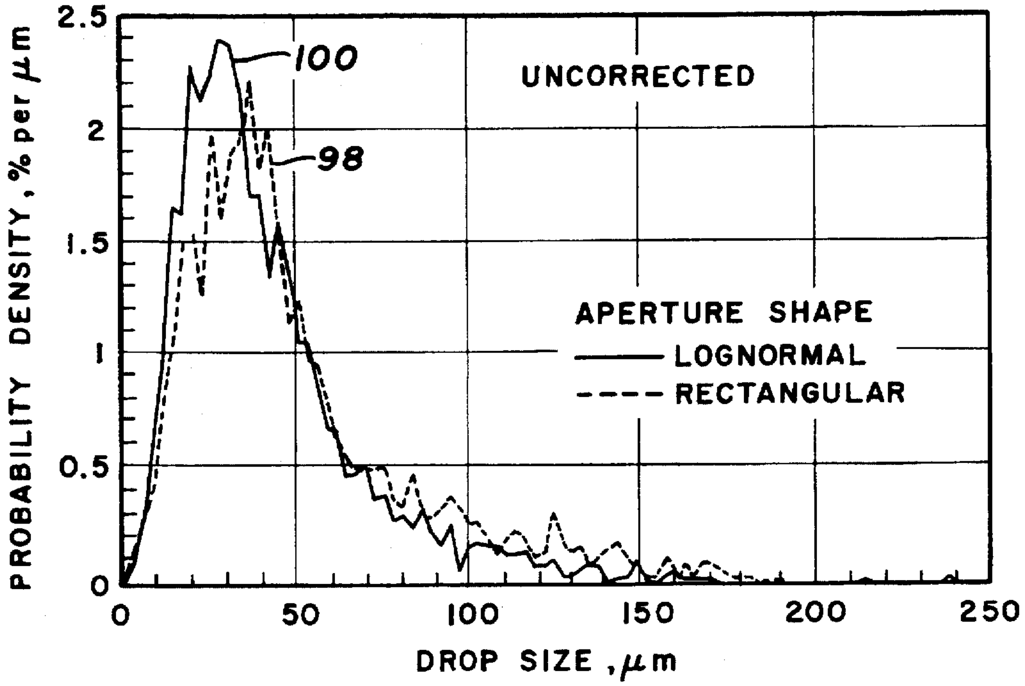
FIG. 15 is a chart comparing droplet size distributions measured with the contoured apertures and the rectangular apertures, respectively.

For the optical setup under consideration, the phase-to-diameter conversion factor of the rectangular apertures was 3.67 degrees per micrometer, i.e. the nominal size range was 360°/3.67=98.2 μm. This factor follows from Equation (63) of Naqwi & Durst ("Light scattering applied to LDA and PDA measurements. Part 1:Theory and numerical treatments", Part. and Part. Syst. Charact., Vol.8, pp.245–258, 1991) for pure refraction. The following optical parameters were used: beam angle, $\alpha$=3.94°; elevation angle, $\psi$=2.11°; wavelength of laser, $\lambda$=0.5145 μm; refractive index of the drops, m=1.33 and off-axis angle, $\phi$=74.74°. In the case of lognormal apertures, the correlation shown in FIG. 10 (curve 86) was used to convert the measured phase shifts into the normalized diameters, which then were multiplied by the nominal diameter to obtain the actual diameters. The resulting size distributions (rectangular at 98 and lognormal at 100) are given in FIGS. 15 and 16. As expected, the rectangular apertures measured larger drops more frequently.

Figure 17:
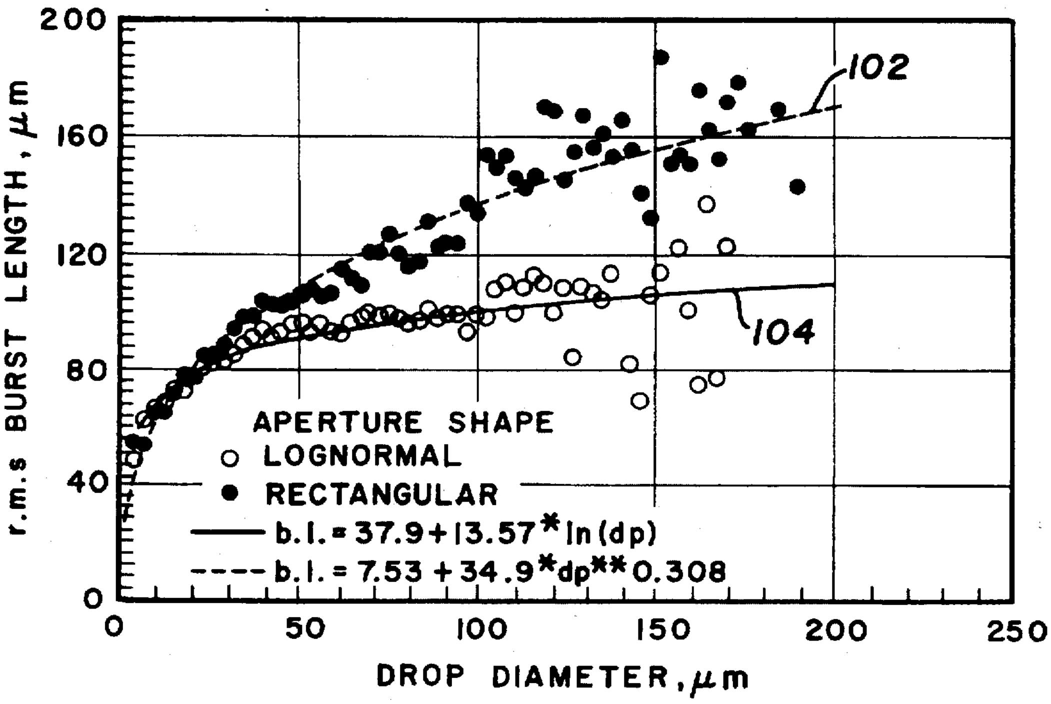
FIG. 17 is a chart comparing root mean square burst lengths as a function of droplet diameter, in alternative cases employing the apertures of FIG. 6 and rectangular apertures with the same geometrical centroids.

FIG. 17 shows root-mean-square (rms) values versus droplet diameters in the case of rectangular apertures indicated at 102, and the lognormal apertures indicated at 104. The rms burst length (defined as the product of particle velocity and signal duration) for a particular size indicates the effective size of the measuring volume for that particular particle size. As seen in the figure, larger particle diameters lead to a more substantial increase in the measuring volume in the case of rectangular apertures, as compared to lognormal apertures. Curves 102 and 104, based on curve fitting to estimate burst lengths (using Table Curve 2D of Jandel Scientific), indicate that over a size range of about 4–200 microns (i.e. a dynamic range of 50:1), the rms burst length increases by a factor of 3.4 for the rectangular apertures. Over the same range, the rms burst length increases by a factor of just 2.3 in the case of lognormal apertures. Thus, the effective measuring volume for the largest particles, when using lognormal apertures instead of rectangular apertures, is reduced by more than 40%. This is accomplished without unduly diminishing the size of the measuring volume for the smallest particles within the range of interest.

As noted above, the use of lognormal apertures causes the signal visibility to decrease with increasing particle diameter. This limits the tendency of signal strength to increase with particle diameters, thus limiting the tendency of the effective measuring volume size to similarly increase. With an appropriate choice of mask 50 to determine the aperture profile, it further is possible to cause the effective measuring volume to decrease as particle diameters increase beyond a critical particle diameter.

Figure 16:
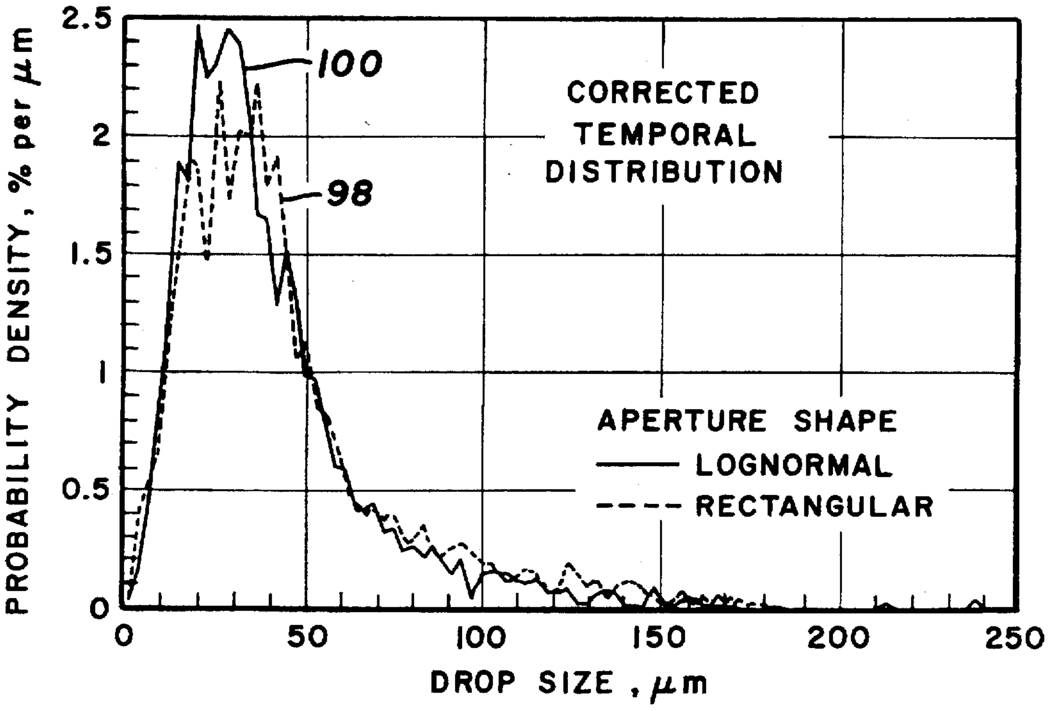
FIG. 16 is a chart showing the size distributions of FIG. 21, with a corrected temporal distribution.

The corrected temporal size distributions, based on the rms burst length information in FIG. 17, are included in FIG. 16. The size distributions measured by the two aperture shapes are shown to agree well after the correction. The residual differences may be caused by the phase shift exceeding 360° and wrapping around during the measurements with the rectangular apertures. The velocity discrimination used to unwrap the phase shifts is rather unreliable.

In the above example, the strong correlation between droplet size and velocity has enhanced the reliability of phase unwrapping in the case of rectangular apertures. In many applications, such correlations do not exist and hence, the ambiguity can be resolved only by using an additional detector.

On the other hand, lognormal apertures extend the size range by a factor of 3 and eliminate the 2π phase ambiguity without adding expensive and cumbersome detection optics and associated electronics.

An Appendix near the end of this Detailed Description explains the theory underlining the shift of the phase centroid relative to the geometric centroid of appropriately shaped apertures, and the derivation of the onion-like shape of apertures **50*a* and 50*b* in system 16**. First, however, several alternative embodiments and their features are discussed.

Figure 18:
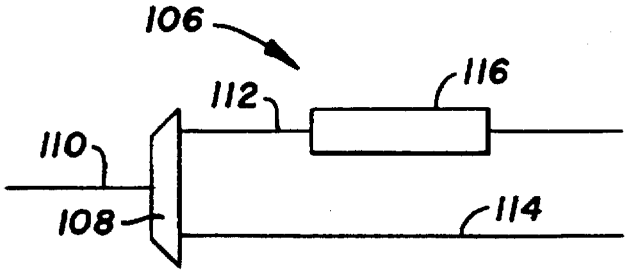
FIG. 18 shows an alternative embodiment beam generating approach to generate moving interference fringes.

FIG. 18 discloses beam conditioning optics 106 of an alternative interferometric measuring system, including a beam splitter 108 receiving a collimated laser beam 110 and generating a pair of collimated beams 112 and 114. Beam 112 is directed through an acousto-optic modulator or Bragg cell 116, which selectively shifts the frequency of laser beam 112 by a predetermined amount, typically 40 MHZ, relative to laser beam 114. The shifted and unshifted beams are provided to fiberoptic cable 24, as before. The frequency shifting causes interference fringes 44 to move in a direction parallel to vector 46 (FIG. 5) and towards the lower frequency beam. This movement of the interference fringes enables detection of the direction as well as velocity of the composite flow, as explained in the Appendix.

Figure 19:
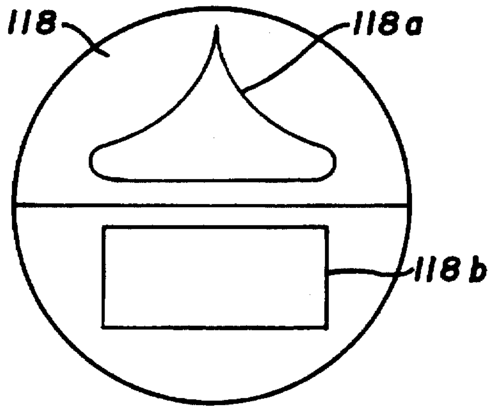
FIG. 19 shows an alternative embodiment detector pair.

FIG. 19 discloses a mask 118 forming a pair of apertures 118*a* and 118*b* for positioning on opposite sides of symmetry plane 42. Aperture 118*a* is selectively contoured for a shape substantially identical to aperture 50*a* in system 16. By contrast, aperture 118*b* has a conventional rectangular profile, although it is matched to aperture 118*a* in the sense that their respective geometric centroids are spaced equally and oppositely from the symmetry plane. The resulting functional relationship between phase differences and particle diameters is non-linear and (with reference to FIG. 10) would appear between curves 84 and 86.

Figure 20:
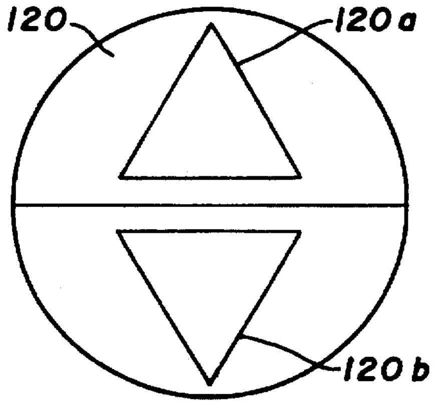
FIG. 20 is a view similar to FIG. 6, illustrating a pair of triangular apertures for receiving scattered coherent energy in an alternative embodiment interferometric particle system.

FIG. 20 shows another alternative mask 120 which determines a pair of triangular apertures 120*a* and 120*b*. Apertures 120*a* and 120*b* are symmetrically positioned about plane of symmetry 42, and are proximate that plane in the sense that non-linear effects occur in the initial 2π cycle of phase differences.

Figure 21:
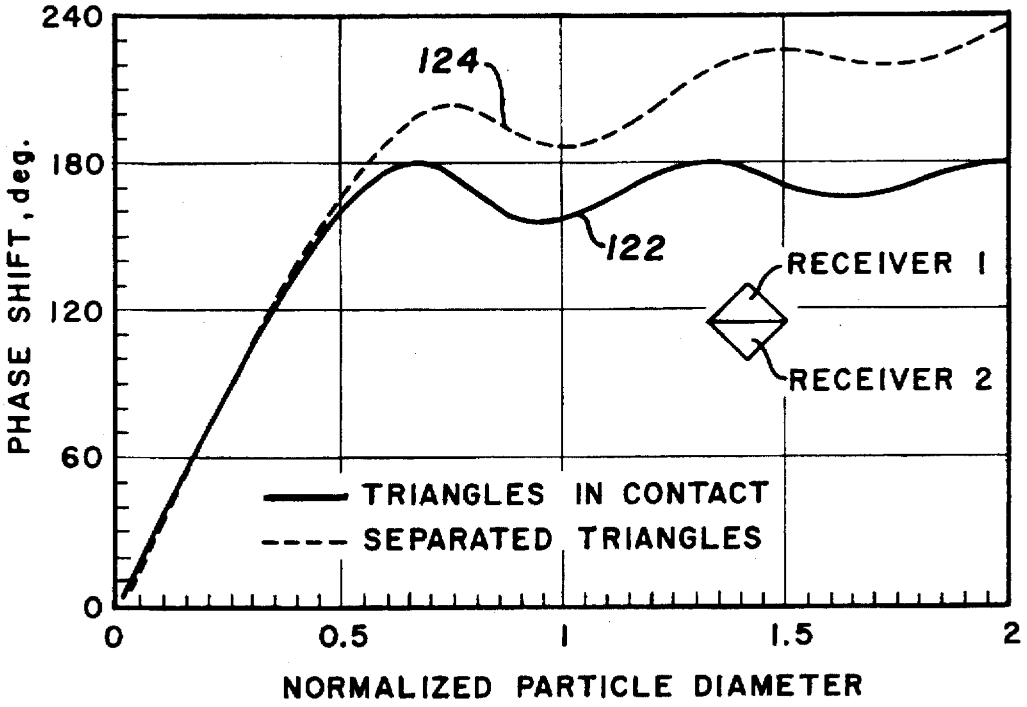
FIG. 21 is a graph similar to FIG. 10 illustrating a non-linear phase/diameter relationship resulting from a pair of triangular apertures.

FIG. 21 shows two curves representing phase diameter functions when triangular apertures are employed. Again, particle diameters are normalized so that the diameter of one unit would coincide with a 360° phase difference for a linear function. Curve 122 is the function for two side-by-side triangular apertures, while curve 124 shows the function for triangular apertures 120*a* and 120*b*, which are slightly spaced apart from one another on opposite sides of the plane of symmetry. More particularly, triangular apertures 120*a* and 120*b* each have a height of 36 mm, and the minimum height over maximum height ($X_{min}/X_{max}$), with both distances taken from the plane of symmetry, is about 0.03.

As seen from curve 122, the phase difference between a pair of side-by-side triangular apertures saturates within the nominal size range and oscillates below 180°. Phase differences corresponding to spaced apart triangular apertures 120*a* and 120*b* exceed 180° beginning at about 0.6 times the nominal diameter. Beyond that point, the slope of curve 124 oscillates and as a whole is substantially more gradual.

tal center line of mask 50.

FIG. 8 illustrates upper portions of mask 50 and receiving lens 54, along with several optical components associated with aperture 50*a*. These include a collimating lens 58 that collimates the diverging energy transmitted through lens 54, and a focusing lens 60 that focuses the collected energy for reception by a fiberoptic cable 64 for transmission to a photodetector 62, e.g. an avalanche photodiode. A similar pair of lenses, associated with aperture 50*b*, provide an optical signal to a fiberoptic cable 66 for transmission to a photodetector similar to detector 62.

The photodetectors convert their optical inputs to respective electrical signals. Further processing circuit components (e.g. mixers, high-pass filters and low-pass filters), indicated generally at 68 in FIG. 1, receive the photodetector outputs and generate sinusoidal electrical analog signals, provided respectively to electrical conductors 70 and 72.

Figure 23:
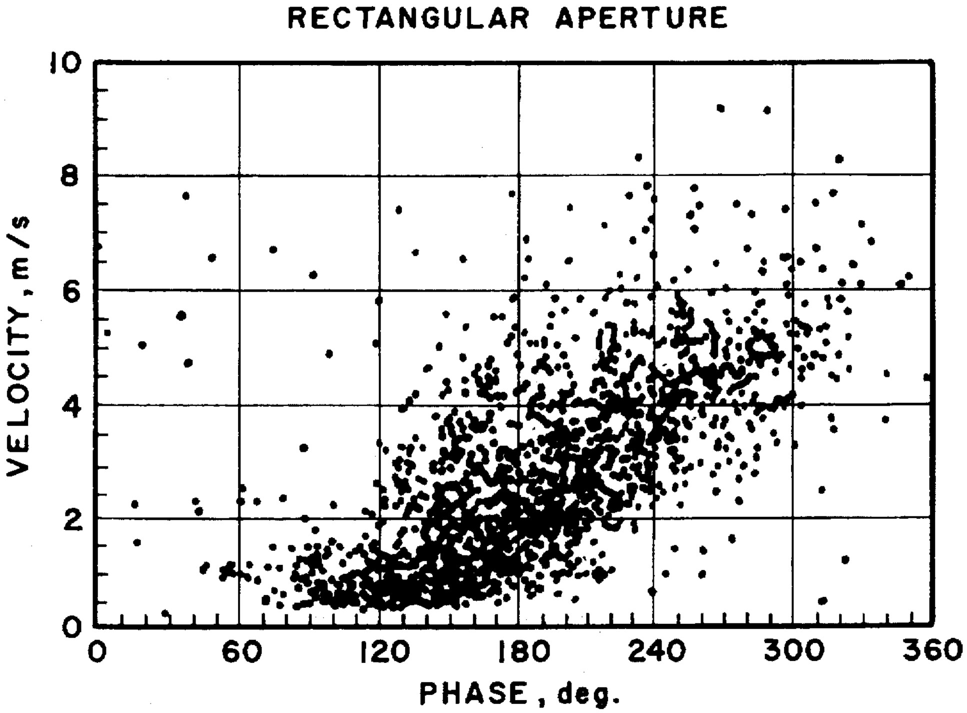
FIG. 23 illustrates multiple point measurements of droplet velocities versus phase shifts, using rectangular apertures having the same geometrical centroids as the triangular apertures.

Electrical signals, taken at points A and B on the conductors, are illustrated in FIG. 9 at 74 and 76, corresponding to apertures 50*a* and 50*b*, respectively. The hori- The results in FIG. 23 are consistent with a linear increase in phase shift as the average velocity (size) increases, confirming a linear phase/diameter relationship in the case of rectangular apertures and illustrating the correlation between droplet sizes and droplet velocities.

Figure 24:
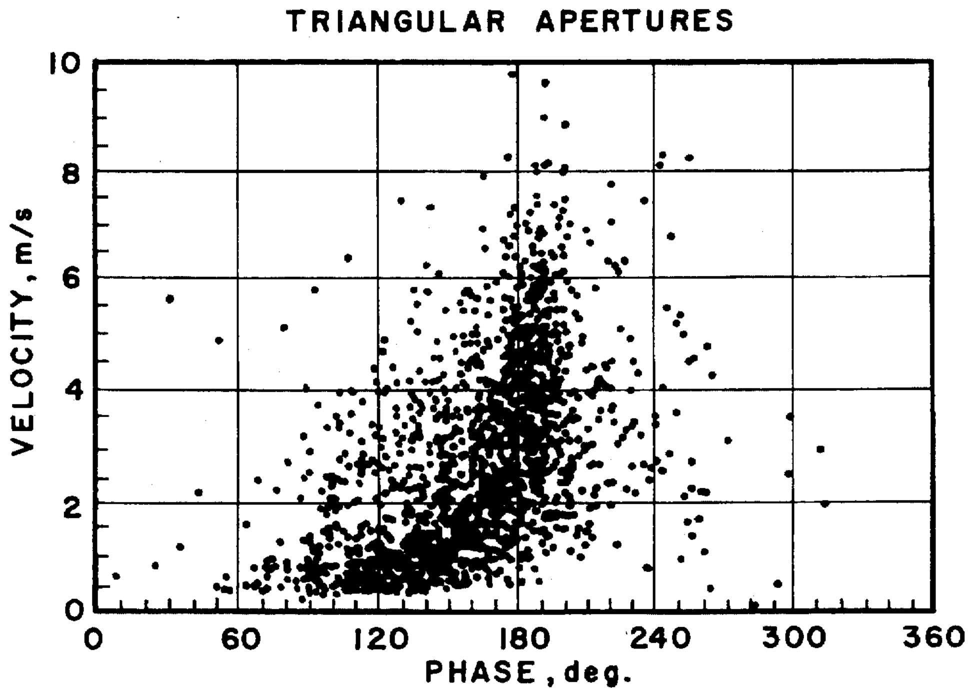
FIG. 24 illustrates multiple measurements of droplet velocity versus phase shift, using the triangular apertures.

By contrast, measurement points in FIG. 24 exhibit saturation of the phase readings slightly above 180°, which verifies the mathematical relationship shown in FIG. 21. The data points in FIG. 24 are based on separated triangular apertures.

Figure 25:
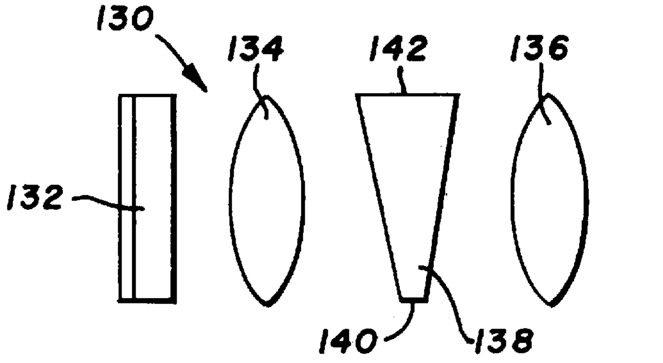
FIG. 25 depicts the optical components of an alternative embodiment detector.

FIG. 25 schematically illustrates an optical detecting arrangement 130 for use in an alternative embodiment measurement system. The arrangement includes a receiving lens 132, a convex collimating lens 134, a convex lens 136 for focusing energy on a photodetector as previously described, and an energy attenuating filter 138 disposed between lenses 134 and 136. Filter 138, while uniform in transmissivity, is graduated in thickness whereby the thickness increases steadily from a minimum value at a bottom edge 140 of the filter, to a maximum value at a top edge 142. Filter 138 thus transmits received energy according to a transmittance pattern characteristic of a triangular aperture or a trapezoidal aperture. It can be appreciated that filter 138 can be shaped with its transmissivity in mind, to yield a transmittance pattern similar to that of apertures 120*a* and 120*b* if desired.

Figure 26:
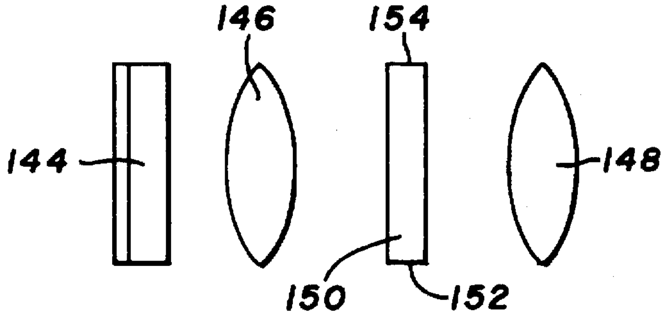
FIG. 26 illustrates the optical components of a further alternative detector.

FIG. 26 illustrates another alternative optical arrangement including a receiving lens 144, convex collimating and focusing lenses 146 and 148, and a filter 150 between the lenses. Filter 150 has a uniform thickness and a transmissivity gradient according to which transmissivity steadily decreases from a bottom edge 152 to a top edge 154. Accordingly, filter 150 can be configured to yield a transmittance pattern similar to that of filter 138 in FIG. 25.

It can be appreciated that more complex shapes and variations in transmissivity can be introduced into attenuation devices such as filters 138 and 150, to yield transmittance patterns similar to that achieved with lognormal apertures 50*a* and 50*b*. Desired transmittance patterns can be achieved through combinations of aperture shape and filter transmissivity and thickness gradients.

Figure 27:
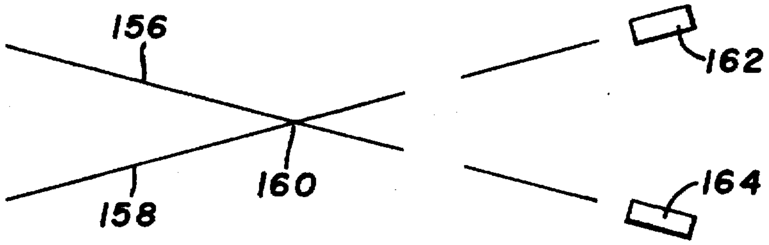
FIG. 27 illustrates an alternative embodiment interferometric particle measuring system featuring planar detection.

FIG. 27 illustrates an alternative interferometric measurement system in which two coherent energy beams 156 and 158 intersect to form a measuring region 160. Scattered energy is collected by two detectors 162 and 164, arranged symmetrically about the plane of symmetry. Detectors 162 ambiguity is avoided over a substantially wider range of particle sizes, due to a non-linear functional relationship between phase difference measurements and particle sizes, as illustrated by a curve 86 in FIG. 10. Over a lower end segment of the size range, i.e. up to about 0.4 times the nominal diameter, curves 86 and 84 have substantially the same slope. Beyond this point, the slope of curve 86 in general decreases as the curve approaches 360°. In fact, the phase difference corresponding to three nominal diameters is just under 360°, showing that the range of particle sizes covered by the initial 2π cycle of phase differences—as compared to the corresponding size range under the linear relationship—is over three times as large.

In FIG. 11, a curve 88 illustrates the decrease in signal visibility as particle sizes within the measuring range increase. In this context, "signal visibility" is defined as the ratio of amplitude fluctuations to the signal base level or pedestal. The amplitude fluctuations are responsive to changes in the intensity of energy received through the apertures as the alternating bright and dark projected fringes of coherent energy beams intersecting to form three beam intersection zones or measuring regions. The measuring regions can overlap or coincide to afford simultaneous measurements that remain distinguishable based on color. Three pairs of detectors, each filtered as to color for correspondence with one of the beam pairs, sense the scattered energy, and generate signals indicative of velocity and phase. Depending on system geometry, the velocity signals can correspond to velocity components in three mutually perpendicular directions. The phase difference readings can provide redundancy as to particle size.

Thus in accordance with the present invention, pairs of coherent energy sensing devices are configured with controlled transmittance of the coherent energy to provide a selected non-linear relationship between measured phase differences and particle sizes, to broaden the range of measurable particles without sacrificing sensitivity in the small diameter segment of the size range, and reducing signal visibility for the larger diameter end of the range to yield more uniform analog signals based on received energy.

The following Appendix explains the theory of controlling aperture transmittance, and more particularly aperture shape, to gain a desired non-linear phase/diameter function.

APPENDIX

A particle velocity component u is obtained from the signal frequency f, based on the equation:

$$f=|f_s+u/d_f| \quad (1)$$

where $f_s$ is the shift frequency and $d_f$ is the fringe spacing. The velocity component u is positive for particle motion opposite to the direction of fringe motion, and vice versa. The shift frequency $f_s$ is normally larger than the term $u/d_f$, so if u is negative the value of measured frequency f is smaller than $f_s$ and vice versa. Hence, Equation (1) allows one to determine the magnitude and direction of the velocity component perpendicular to the fringes.

For a coherent light wavelength λ, the fringe spacing is found using the equation:

$$d_f=\lambda/2\sin\alpha. \quad (2)$$

Thus, the signal frequency relates to a component of particle velocity. Likewise, phase shift relates to the particle size. To illustrate this latter relationship, some background information is provided below.

The fringes in the measuring region are projected by scattering onto the front plane of the receiving device 52, whereby the light energy in the scattered fringes is collected over regions of space defined by the apertures **50*a* and 50*b*. These apertures are a part of the receiving device 36**, which may also incorporate optical attenuators with varying transmittance over the open portions of the apertures.

Figure 30:
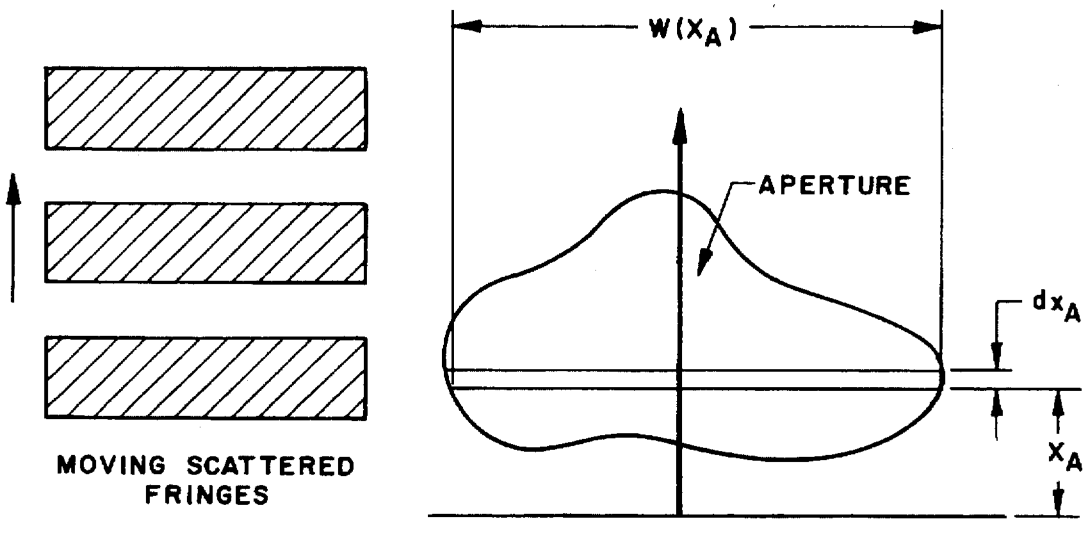
FIG. 30 illustrates an arbitrarily shaped aperture and adjacent scattered interference fringes.

As the particle moves in the measuring volume, the scattering fringes 82 (see FIG. 30) move across the apertures 56 and 58, so that the signal arrives earlier on one receiver and later on the other.

A receiving aperture with an arbitrarily varying width w(x) is considered in FIG. 3, where x-axis is perpendicular to the scattered fringes. The scattered light power collected by a segment of thickness $dx_A$ may be expressed as $$dP_s=C_P w(x_A)t(x^A)\,[1\cos(\omega_D t+\Delta\phi)]dx_A \quad (3)$$

where $C_P$ is a constant that has units of intensity. The above equation represents the response of a point detector at a particular x location. In a common phase Doppler setup, the scattered fringe spacing $s_f$ decreases with the increasing particle size and is directly proportional to the curvature of the particle surface. For a point detector at x, the signal phase Δφ is given as $$\Delta\phi=2\pi x_A/s_f \quad (4)$$

The total scattered light signal is obtained by integrating Equation (3) over the entire aperture. This discussion is specialized to the case where transmittance $t(x_A)$ is uniform, i.e. an attenuator is not used in the filtration device, so that the total scattered power is given as $$P_s=P+F\cos(\omega_D t+\overline{\Delta\phi}) \quad (5)$$

where P and F are the pedestal and the amplitude of fluctuation respectively. These are given as $$P=C_P\int_{x_{Amin}}^{x_{Amax}} w(x_A)dx_A \quad (6)$$

and $$F=C_P\sqrt{\left(\int_{x_{Amin}}^{x_{Amax}} w(x_A)\cos(2\pi x_A/s_f)dx_A\right)^2+\left(\int_{x_{Amin}}^{x_{Amax}} w(x_A)\sin(2\pi x_A/s_f)dx_A\right)^2}. \quad (7)$$

In most phase Doppler processors, the signals are high-pass filtered prior to measurement of phase shift and frequency, so that the pedestal (low frequency component) is removed and the filtered signals can be represented by Equation (5) without the first term on the right hand side. Hence, the amplitude of fluctuation F represents the signal strength as seen by the processors.

The total phase shift $\overline{\Delta\phi}$ is represented by $$\sin\overline{\Delta\Phi}=\frac{C_p}{F}\int_{x_{Amin}}^{x_{Amax}} w(x_A)\sin(2\pi x_A/s_f)dx_A \quad (8)$$

and $$\cos\overline{\Delta\Phi}=\frac{C_p}{F}\int_{x_{Amin}}^{x_{Amax}} w(x_A)\cos(2\pi x_A/s_f)dx_A. \quad (9)$$

The signal visibility, defined as the ratio of the fluctuation amplitude to the signal pedestal, may be expressed as $$V=\frac{\sqrt{\left(\int_{x_{Amin}}^{x_{Amax}} w(x_A)\cos(2\pi x_A/s_f)dx_A\right)^2+\left(\int_{x_{Amin}}^{x_{Amax}} w(x_A)\sin(2\pi x_A/s_f)dx_A\right)^2}}{\int_{x_{Amin}}^{x_{Amax}} w(x_A)dx_A}. \quad (10)$$

Figure 2:
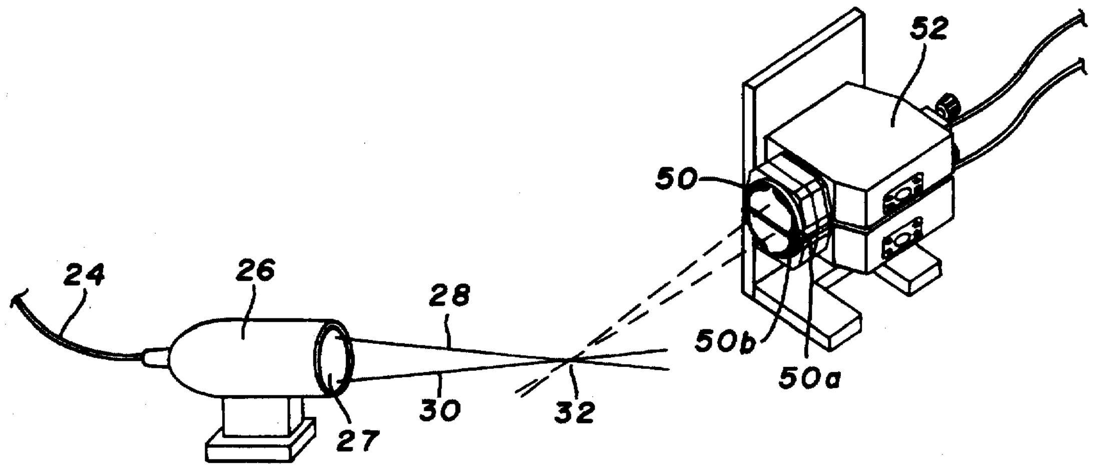
FIG. 2 is a partial view of the system in FIG. 1, showing illumination and energy detecting components.

The phase difference between two symmetrically located receivers, as shown in FIG. 2, is given as $$\Delta\phi_{12}=2\overline{\Delta\phi}. \quad (11)$$

For small values of phase angles, i.e. for large $s_f$ or small particles, $$\overline{\Delta\Phi}=2\pi\bar{x}_A/s_f, \tag{12}$$

where $x_A$ represents the geometrical centroid of the aperture, given by $$\bar{x}_A=\frac{\int_{x_{Amin}}^{x_{Amax}} w(x_A)x_A dx_A}{\int_{x_{Amin}}^{x_{Amax}} w(x_A)dx_A}. \tag{13}$$

The phase diameter relationship represented by Equations (12) and (13) is obtained by representing the tangent and sine of the pertinent angles by the angles themselves and setting the cosine to 1. Similarly, using first two terms in the power expansion of sine and cosine functions the signal visibility may be expressed as $$V=1-2\left(\frac{\pi}{s_f}\right)^2(\overline{x_A^2}-\bar{x}_A^2), \tag{14}$$

where $$\overline{x_A^2}=\frac{\int_{x_{Amin}}^{x_{Amax}} w(x_A)x_A^2 dx_A}{\int_{x_{Amin}}^{x_{Amax}} w(x_A)dx_A}. \tag{15}$$

Thus, visibility approaches 1 with decreasing particle diameter (i.e. increasing $s_f$) with narrowing aperture width along $x_A$-axis.

Comparing Equation (12) with (4), the phase shift for the finite aperture is identical to that of a point detector at the centroid of the aperture. For small particles, the phase centroid of a finite aperture is represented by a fixed point, i.e. the geometrical centroid of the aperture regardless of its shape.

However, according to Equations (8) and (9), location of the effective point detector may vary with the particle diameter for larger values of diameter $d_p$. Equations (8)–(10) for phase and visibility are solved below for certain standard aperture shapes.

Rectangular apertures

Figure 22:
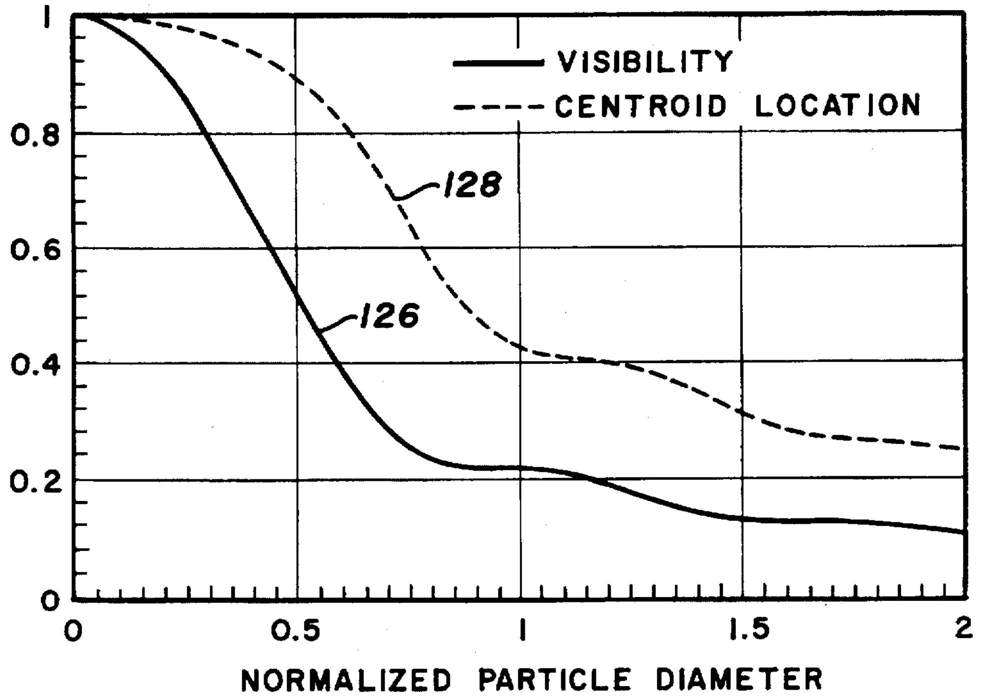
FIG. 22 is a chart illustrating signal visibility as a function of normalized diameter, in the case of triangular apertures.

A rectangular aperture is characterized by the constant value of the width $w(x_A)$, so that the integrals in Equations (8)–(10) are easily evaluated. The results can be expressed FIG. 22 illustrates at 126 the decrease in signal visibility as particle diameters increase, in the case of triangular apertures in the side-by-side arrangement. Curve 128 illustrates the shift of the phase centroid away from the geometric centroid as particle diameters increase. The value of one at low particle diameters indicates that initially the phase centroid and geometrical centroid coincide. In a triangular aperture the geometric centroid is at one-third of the height and centered between the two opposed sides. Curve 128 indicates movement of the phase centroid toward the plane of symmetry as particle diameters increase.

FIGS. 23 and 24 show multiple points relating water droplet velocities and phase measurements, in the cases of rectangular apertures and triangular apertures, respectively. As mentioned previously in connection with FIGS. 12 and 13, droplet velocity increases with size, and thus is a reliable indicator of droplet size. The rectangular apertures used in the test have the same geometric centroids (in terms of distance from plane of the symmetry) as the triangular apertures.

For normal applications of rectangular apertures, $\Delta x_A$ is kept smaller than the smallest value of $s_f$, which corresponds to the largest particle. In this case, $$\overline{\Delta\Phi}=2\pi\bar{x}_A/s_f \tag{20}$$

With increasing particle diameters, as $s_f$ equals $\Delta x_A$, the signal visibility vanishes according to Equation (18). For even smaller values of $s_f$, the common factor in Equations (16) and (17) is negative, so that the phase is shifted by 180°, i.e.

$$\overline{\Delta\Phi}=\frac{2\pi\bar{x}_A}{s_f}-\pi=\frac{2\pi}{s_f}\left(\bar{x}_A-\frac{s_f}{2}\right) \tag{21}$$

Evidently, phase jumps of 180° occur at the integral values of $\Delta x_A/s_f$. According to Equation (18), the signal visibility vanishes at the point of each phase jump. For very small particles (or large $s_f$), the phase centroid is fixed and coincides with the geometrical centroid. It is shifted down abruptly by $s_f/2$ at the first phase jump and shifted up at the second jump.

With increasing particle diameter (i.e. decreasing $s_f$) the first phase jump occurs when the scattered fringe spacing $s_f$ reaches the height of the aperture $\Delta x_A$. Under this condition, the receiving aperture is continuously exposed to a complete scattered bright fringe and a complete dark fringe. Hence, the total amount of light collected by the receiver is unaffected by the motion of the scattered fringes. Consequently, the collected scattered light does not exhibit any oscillations, thus signal visibility is zero.

Figure 31:
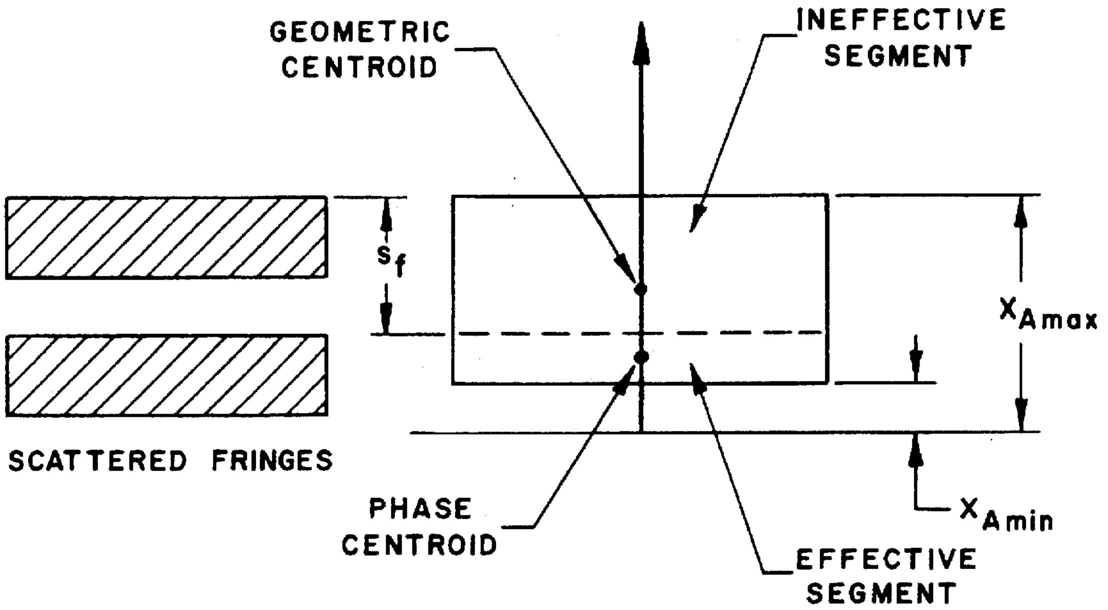
FIG. 31 illustrates a rectangular aperture and adjacent scattered interference fringes.

As the scattered fringe spacing is reduced below the aperture height, the receiving aperture may be considered as composed of two segments effective and ineffective segments. The height of the ineffective segment equals the scattered fringe spacing, so that it does not contribute to the oscillations in the signal. The remaining aperture portion is the effective segment, which is responsible for modulation of the signal. The geometrical centroid of the effective segment may be regarded as the phase centroid of the aperture, as shown in FIG. 31. Equation (21) is based on the assumption that the ineffective segment occupies the upper portion of the aperture, so that the phase centroid is shifted down after the phase jump. Alternatively, if the ineffective segment is considered as the lower part of aperture, there is an upward shift in the phase centroid. The two alternative descriptions lead to phase diameter relations that differ by a and 164 lie within the beam plane. In other words, the offset angle $\phi$ (FIG. 4) is zero. This planar arrangement is particularly advantageous for characterizing cylindrical objects, e.g. drawn fibers.

Figure 28:
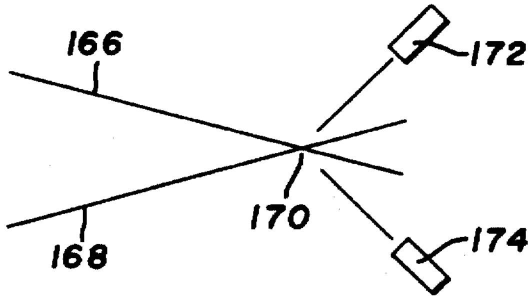
FIG. 28 illustrates an alternative embodiment particle measurement system with increased detector elevation angles.

FIG. 28 discloses a further alternative interferometric measuring system with two laser beams 166 and 168 forming a measuring region 170 at their intersection. Two detectors 172 and 174 are remote from the symmetry plane in the sense that the elevation angle $\psi$ (FIG. 3) is on the order of about 10°, and the non-linearity of the phase/diameter function occurs within a subsequent cycle of phase differences, i.e. a cycle consisting of phase differences greater than 360°. This arrangement is suitable for characterizing larger diameter particles, for example with the diameters exceeding 100 microns.

In a further alternative embodiment not illustrated, particles can be measured to determine velocity components in several different directions simultaneously. In this arrangement, three different wavelengths of coherent energy (e.g. green, blue and violet) are used to provide three pairs As explained below, the shifts in the phase centroid—in the case of non-rectangular apertures—may be substantial and may occur gradually with increasing particle diameter.

Trapezoidal Apertures

A trapezoidal aperture has the simplest shape that offers a variable width w $(x_A)$. Response of this aperture is examined to illustrate the gradual shifts in the phase centroid that may occur with increasing particle size.

Figure 32:
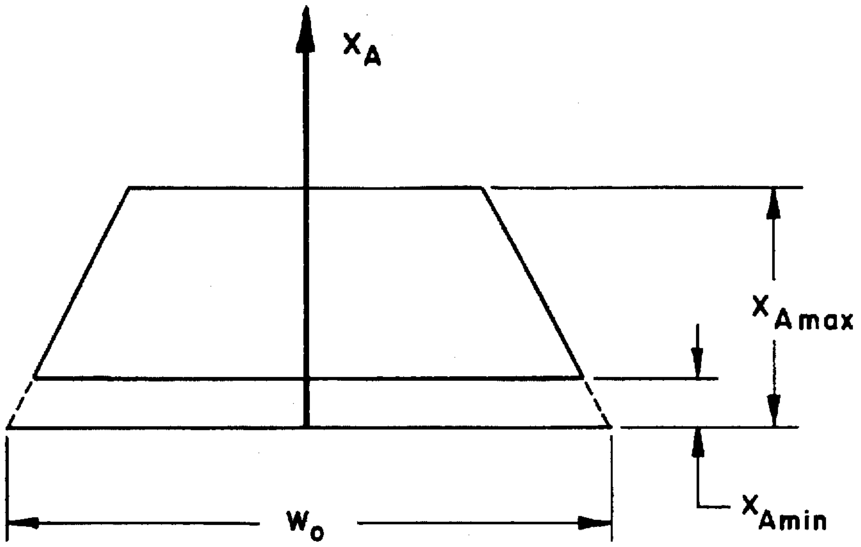
FIG. 32 illustrates a trapezoidal aperture.

The width of a trapezoidal aperture, as shown in FIG. 32, is given by $$w(x_A)=x_0-s_w x_A,\ x_{Amin} \geqq x_A \geqq x_{Amax}, \qquad (22)$$

where $x_{Amin} \leqq 0$, $w_0 \leqq 0$ and in the case of positive $s_w$, $x_{Amax} \geqq w_0 s_w$. The symbol $s_w$ represents slope. In limiting cases, this aperture may be reduced to a triangle or an inverted triangle with its vertex in the plane of symmetry.

Substituting Equation (22) into Equation (8), the following expression is obtained for the sine of the phase shift:

$$\frac{2\pi F}{C_p s_f} \sin\overline{\Delta\Phi} = w_0\,[\cos(2\pi x_{Amin}/s_f) - \cos(2\pi x_{Amax}/s_f)] + S_w[x_{Amax}\cos(2\pi x_{Amax}/s_f) - x_{Amin}\cos(2\pi x_{Amin}/s_f)] - \frac{S_w s_f}{2\pi}\,[\sin(2\pi x_{Amax}/s_f) - \sin(2\pi x_{Amin}/s_f)] \qquad (23)$$

Similarly, by substituting Equation (22) into Equation (9), the cosine of the phase shift is expressed as $$\frac{2\pi F}{C_p s_f} \cos\overline{\Delta\Phi} = w_0\,[\sin(2\pi x_{Amax}/s_f) - \sin(2\pi x_{Amin}/s_f)] - S_w[x_{Amax}\sin(2\pi x_{Amax}/s_f) - x_{Amin}\sin(2\pi x_{Amin}/s_f)] - \frac{S_w s_f}{2\pi}\,[\cos(2\pi x_{Amax}/s_f) - \cos(2\pi x_{Amin}/s_f)] \qquad (24)$$

The above relations can be reduced to Equations (16) and (17) for $s_w=0$, i.e. a rectangular aperture.

For a trapezoidal aperture, the signal pedestal as given by Equation (6) reduces to $$P=C_P(x_{Amax}-x_{Amin})[w_0-s_w(x_{Amax}+x_{Amin})/2]. \qquad (25)$$

The response of a trapesoidal aperture may be expressed in terms of three independent parameters, i.e. $2\pi x_{Amax}/s_f$, $x_{Amin}/x_{Amax}$ and $s_w s_{Amax}/w_0$. A triangular aperture may be defined by assigning the values of 0 and 1 to the second and third parameter respectively. The phase shift for this triangular aperture is examined below. Later, the effects of perturbations in the second and third parameter are examined.

For the triangular aperture, Equations (23)–(25) are reduced to the following relations:

$$\frac{2\pi F}{C_p s_f w_0} \sin\overline{\Delta\Phi} = 1 - \mathrm{sinc}(3\pi d_p^*); \qquad (26)$$

$$\frac{2\pi F}{C_p s_f w_0} \cos\Delta\Phi = \frac{1-\cos(3\pi d_p^*)}{3\pi d_p^*}\ ; \qquad (27)$$

$$P = C_p w_0 x_{Amax}/2. \qquad (28)$$

$$P=C_p w_0 x_{Amax}/2. \qquad (28)$$

Using Equations (26)–(28), the signal visibility, as defined by Equation (8), is expressed as $$V=\frac{\sqrt[2]{9\pi^2 d_p^{*2} + 2(1-\cos 3\pi d_p^*) - 6\pi d_p^* \sin 3\pi d_p^*}}{9\pi^2 d_p^{*2}}, \qquad (29)$$

where non-dimensional particle diameter (chosen to equal 1 at 360°) is:

$$d_p^* = \frac{2\bar{x}_A}{s_f}\ . \qquad (30)$$

The symbol $x_A$ represents the geometrical centroid of the triangular aperture, so that $x_A=x_{Amax}/3$.

The non-dimensional diameter would be 1 for $\Delta\phi_{12}=360°$, provided that the phase centroid is fixed at the geometrical centroid, i.e. the initial slope of the phase diameter curve is maintained. The size range $0 \leqq d_p \leqq 1$ will be hereafter referred to as the nominal size range. As shown later, shaped apertures allow the 360 degree limit to be extended to as large a value of $d_p$ as 3.

According to Equation (4), location of the phase centroid $x_A$ is given by $$\tilde{x}_A = \frac{\overline{\Delta\Phi}}{2\pi}\, s_f = \frac{\overline{\Delta\Phi}}{3\pi d_p^*}\, x_{Amax}. \qquad (31)$$

Since $x_A=x_{Amax}/3$, the relationship between phase centroid and geometrical centroid may be expressed as $$\frac{\tilde{x}_A}{\bar{x}_A} = \frac{\overline{\Delta\Phi}}{\pi d_p^*}\ . \qquad (32)$$

FIGS. 21 and 22 show the phase shift, visibility and the centroid location for the triangular aperture.

The phase shift between a pair of triangular apertures saturates within the nominal size range and oscillates below 180°. As obvious from Equation (27), $\overline{\Delta\phi}$ is 90° for $d_p$=⅔, 4/3, 2, . . . as the cosine of $\overline{\Delta\phi}$ vanishes at these points. Consequently, $\Delta\phi_{12}$ is 180° at the above values of $d_p$, as shown in FIG. 21. It is also clear from FIG. 21 as well as Equations (26) and (27) that the limiting value of phase shift for very large diameters is 180°.

According to FIG. 22, signal visibility decreases gradually for a triangular aperture but does not vanish completely. The phase centroid is initially located at the geometrical centroid, i.e. $\tilde{x}_A/\bar{x}_A=1$. With the increasing particle diameter, it shifts down for the upper aperture and up for the lower aperture.

FIG. 22 also includes the case of triangular apertures that are separated, so that $x_{Amin}/X_{Amax}=0.03$.

Aperture Shape for an Arbitrary Response Curve

Given a linear relationship for point detectors, non-linear phase diameter relationships can be obtained using aperture shapes that are significantly different from a rectangle. Nonlinear response curves are desirable for the following reasons:

(i) they extend the size range while maintaining a high sensitivity to small particles;

(ii) they provide a uniform percent-of-the-reading sensitivity, i.e. an invariant value of $$S_{por} = \frac{d(2\overline{\Delta\Phi})}{100\,d(d_p)/d_p} \qquad (33)$$

for a pair of symmetric receivers;

(iii) they eliminate the 2π ambiguity (i.e. the inability to distinguish between a phase shift φ and 2π+φ) by ensuring that the phase shift does not exceed 360°.

To meet the above requirements, one needs to calculate the aperture shape $w(x_A)$ for a given phase/diameter relationship $\overline{\Delta\phi}(d_p)$. By multiplying Equation (8) with $\sqrt{-1}$ and adding to Equation (9), the integral can be expressed in the following form $$\exp[i\overline{\Delta\Phi}(d^*_p)] = \int_{-\infty}^{+\infty} w^*(x^*_A)\exp(2\pi i d^*_p x^*_A)dx^*_A, \tag{34}$$

where the non-dimensional particle diameter is defined by Equation (30). Furthermore, a non-dimensional aperture width and height are introduced and defined as below:

$$w^* = \frac{2\bar{x}_A C_p}{F}\, w, \tag{35}$$

$$x^*_A = \frac{x_A}{2\bar{x}_A}\,. \tag{36}$$

The distance along the $x_A$-axis is normalized with the spacing between the geometrical centroids of two symmetrically located apertures. The above formulation allows one to treat the relationship between the aperture and the response curve as a Fourier transform.

In order for w to be real, the left hand side of Equation (34) must exist for both the positive and negative values of $d_p$ and must satisfy the following relationship (see Press et al, Numerical Recipes, Chap. 12, Cambridge University press, 1986):

$$\overline{\Delta\Phi}(-d^*_p) = -\overline{\Delta\Phi}(d^*_p). \tag{37}$$

Of course, the negative particle diameters do not have any physical significance; however, extension of the phase diameter relationship to the negative sizes allows one to use the Fourier transform for solving the inverse problem. Inverting the transform in Equation (34), $$w^*(x^*_A) = \int_{-\infty}^{\infty} \exp[i\overline{\Delta\Phi}(d^*_p)]\exp[-2\pi i d^*_p x^*_A]d(d^*_p). \tag{38}$$

Note that $w^*(x^*_A)$ is a delta function if the phase diameter relationship is linear, i.e. the above formulation readily allows one to recover the point detector arrangement.

For some phase diameter relations, the corresponding function $w^*(x^*_A)$ may become negative for certain values of $x^*_A$, indicating that a realizable aperture shape does not exist. However, the exponential response curve discussed (8)-(10) are easily evaluated. The results can be expressed as follows, where "sinc" is the sine divided by the angle, in radians:

$$\sin\overline{\Delta\phi} = \sin(2\pi x_A/s_f)\cdot\sin(\pi\Delta x_A/s_f) + |\sin(\pi\Delta x_A/s_f)| \tag{16}$$

$$\sin\overline{\Delta\phi} = \sin(2\pi x_A/s_f)\sin(\pi\Delta x_A/s_f) + |\sin(\pi\Delta x_A/s_f)| \tag{17}$$

and $$V = \frac{s_f}{\pi\Delta x_A}\left|\sin\left(\frac{\pi\Delta x_A}{s_f}\right)\right| = \left|\mathrm{sinc}\left(\frac{\pi\Delta x_A}{s_f}\right)\right|; \tag{18}$$

where $$\Delta x_A = x_{Amax} - x_{Amin}. \tag{19}$$

According to Equations (16) and (17), phase shift can be given by an equation of the form (12), provided that the second factor, i.e. the common factor, on the right hand side of Equations (16) and (17) has a positive sign.

Figure 29:
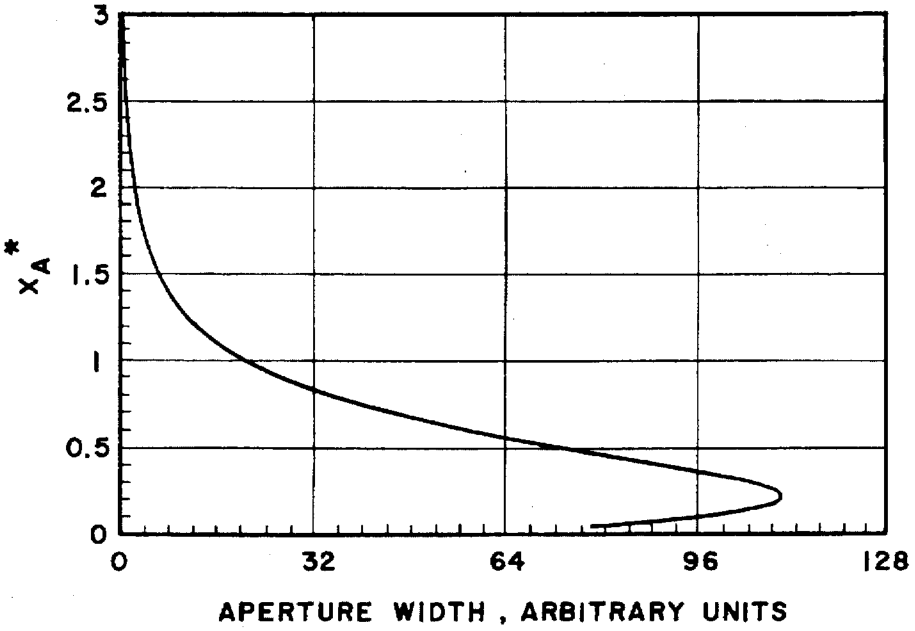
FIG. 29 is a chart showing an aperture contour corresponding to an exponential relationship between phase shift and particle size, computed using a Fourier transform method.

By extending the phase diameter relationship of Equation (39) to the negative diameters, in accordance with Equation (37), a fast Fourier transform (FFT) algorithm can be used to compute the corresponding width function. The results are shown in FIG. 29. The boundary of the aperture is characterized by a combination of convex and concave segments. Such an aperture geometry has not been used in the prior art. The aperture shape is fairly simple and may be approximated by a lognormal function.

Based on the above considerations, pairs of symmetrically located lognormal apertures are analyzed below in detail.

Lognormal Apertures

It is understood that the response of the aperture in FIG. 33 would be unaffected if it is made symmetric by mirror imaging its contour about $x_A$-axis. The resulting aperture is shaped like an "onion" or a "tear drop", such as the shape depicted in FIG. 33. Such shapes can be implemented conveniently in practice. The lognormal apertures considered hereafter have symmetric onion-like shape.

A lognormal function has two independent variables. Four independent variables are needed if the coordinates of the lognormal function are shifted arbitrarily. Such a function may be expressed as $$w = \frac{A_{lgn}}{(x_A + x_{A0})}\exp\left\{-\frac{1}{2\sigma^2_{lgn}}[\ln(x_A + x_{A0}) - \mu_{lgn}]^2\right\} - \Delta w, \tag{41}$$

$$x_{Amin} \leqq x_A \leqq 1.$$

The above aperture can be specified in terms of four parameters, i.e.

(in) $x_{Amin}$: the minimum value of normalized $x_A$, so that the maximum value is 1;

(ii) $x_{A0}$: the zero-shift of lognormal distribution along $x_A$-axis;

(iii) $x_{Ap}$: location of the maxima of the aperture width;

(iv) $\sigma_{lgn}$: width of the lognormal distribution.

Normalizing the maximum width of the aperture to 1, the parameters $A_{lgn}$, $\mu_{lgn}$ and $\Delta w$ may be obtained from the relations:

$$\mu_{lgn} = \sigma^2_{lgn} + \ln(x_{Ap} + x_{A0}); \tag{42}$$

$$\frac{1}{\Delta w} = (1 + x_{A0})\exp\left\{\frac{1}{2\sigma^2_{lgn}}\left[\ln\left(\frac{1 + x_{A0}}{x_{Ap} + x_{A0}}\right) - \sigma^2_{lgn}\right]^2 - \right. \tag{43}$$

descriptions lead to phase diameter relations that differ by a complete cycle, i.e. $2\pi$ radians.

The above discussion clarifies the mechanism that causes the shift in the phase centroid. With decreasing $s_f$, a portion of the receiving aperture is "blinded" as it collects a fixed amount of light despite the motion of the scattered fringes. Such ineffective segments appear abruptly in the case of a rectangular aperture, because the shape of the aperture agrees with the shape of the scattered fringes. In the case of a non-rectangular aperture, the ineffective segments emerge gradually, i.e. the phase centroid is shifted gradually. Consequently, the signal visibility does not vanish completely.

In the case of a rectangular aperture, it is desirable to design the aperture such that the entire size range of interest lies in the first lobe of the visibility curve, to avoid the zero visibility condition. As a consequence, it suffices to treat the geometrical centroid as the phase centroid. In the earliest phase Doppler systems, the receiving apertures were nearly rectangular. This is why the shifts in the phase centroid were ignored in the early works on the technique.

This shape is depicted in FIG. 7. The geometrical centroid of this aperture is located at $x_A$=0.3097. The corresponding response curve, signal visibility and percent-of-the-reading sensitivity are given in FIGS. 10 and 11. It can be seen that the size range is extended by a factor of three as compared to the nominal size range. Furthermore, the visibility is always non-zero and large enough to produce measurable signals. The sensitivity is such that over most of the size range, about 1° phase shift is obtained for 1% variation in the size.

Reduction in the signal visibility with increasing particle diameter is, in fact, a desirable feature of phase Doppler technique. The signal strength is known to increase with the square of the particle diameter. However, due to decreasing visibility, the amplitude of fluctuation F does not increase so excessively. As explained earlier, parameter F represents the signal strength seen by the signal processor. Uniform signal strength allows more uniform bit-resolution for the digitized signals, so that all the signals are processed with about the same precision. In the case of analog processors, the output of analog components varies with the signal amplitude. This source of uncertainty is suppressed if the signal amplitude is more uniform.

Another adverse effect of large variations in the signal strength is discussed by Naqwi ("Innovative Phase Doppler Systems and their Applications", Part. Part. Syst. Charact., Vol.11,pp.7–21, 1994) who has taken into consideration the effects of non-uniform illumination of the particle, due to a bell-shaped (Gaussian) laser intensity distribution in the measuring volume. With increasing signal strength, it is possible to detect signals from the particles that cross only the outer layers of the measuring volume, where illumination is highly non-uniform. Hence, the measurements are less prone to error if the signal strength is rather uniform over a wide range of particle diameters.

As discussed by Saffman ("Automatic calibration of LDA measurement volume size", applied Optics, Vol. 26, pp.2592–2597, 1987), the root-mean-square (rms) value of the burst length (mm) in a size bin is a measure of the effective size of the measuring volume for that bin. The burst length value is defined as the product of particle velocity and the signal duration; both of these parameters were recorded. According to FIG. 17, the effective measuring volume increases more significantly with the particle diameter for the rectangular apertures, as opposed to the lognormal apertures.

What is claimed is:

1. An apparatus for non-contact measurement of light scattering elements including:

a beam generating means for generating two linearly propagating beams of coherent energy oriented at a predetermined beam angle relative to one another and intersecting one another to define a beam plane said beams interfering with one another over a measuring region to form interference fringes extending across the measuring region in parallel fashion;

an alignment means operatively associated with the beam generating means for positioning the beams with respect to a composite flow so that light scattering elements within the composite flow move through the measuring region;

an energy detecting means for sensing the coherent energy scattered by each of the light scattering elements as it traverses the measuring region, said detecting means including first and second detectors at respective first and second locations spaced apart from the measuring region, said detectors having respective first and second energy receiving apertures, said energy detecting means generating respective first and second detector signals responsive to the energy received through the first and second apertures, respectively, wherein said coherent energy received at each of the apertures forms a projection of said interference fringes traveling across the aperture in a fringe movement direction normal to a lengthwise extension of the projected fringes;

a data generating means for generating size information in response to receiving the first and second detector signals, said data generating means including a signal processing means for generating phase difference values representing temporal shifts between the first and second detector signals, and a conversion means for generating said size information based on the phase difference values; and wherein at least the first detector includes a coherent energy filtration means for determining a transmittance pattern controllably varying the transmittance of the coherent energy in said fringe movement direction whereby said phase difference values, when generated responsive to light scattering elements having sizes within a selected size range, are generated according to a non-linear function over at least a part of a 2π cycle of the phase values that corresponds to the selected size range;

and said conversion means generates said size information substantially according to said non-linear function.

2. The apparatus of claim 1 wherein:

the coherent energy filtration means comprises an opaque mask with a selectively shaped opening therethrough, wherein the transmittance pattern is determined by the shape of said opening.

3. The apparatus of claim 2 wherein:

the opening through the mask is triangular.

4. The apparatus of claim 2 wherein:

said opening through the mask has a shape defined by two opposite side boundaries extending between a minimum height and a maximum height of the opening with the height measured in said fringe movement direction, the side boundaries are contoured to define a width, in the direction of said lengthwise extension of the projected fringes, that varies over the height, and a maximum width of the opening is located between the maximum height and the minimum height and is greater than the width at said maximum height and minimum height.

5. The apparatus of claim 4 wherein:

said side boundaries are contoured according to a lognormal function.

6. The apparatus of claim 1 wherein:

the coherent energy filtration means includes an energy attenuation device having a transmittance of the coherent energy that varies in said fringe movement direction to determine the transmittance pattern.

7. The apparatus of claim 1 wherein:

said phase values are generated substantially according to a substantially linear function determined by a substantially constant ratio ϕ/d of phase difference values to diameters over a lower segment of said selected size range, and according to said non-linear function over an upper segment of the selected size range.

8. The apparatus of claim 1 wherein:

said second detector includes a coherent energy filtration means for determining a transmittance pattern controllably varying the transmittance in said fringe movement direction, with said transmittance patterns of the first and second detectors cooperating to determine the non-linear function.

9. The apparatus of claim 8 wherein:

a plane of symmetry orthogonal to the beam plane and bisects the beam angle intersects the beam plane and the first and second apertures are located on opposite sides of the plane of symmetry.

10. The apparatus of claim 9 wherein:

the first and second apertures are arranged symmetrically about the symmetry plane.

11. The apparatus of claim 10 wherein:

the respective transmissivity patterns of the first and second detectors are substantially the same, and symmetrical about the plane of symmetry.

12. The apparatus of claim 10 wherein:

said first and second apertures are disposed proximate the symmetry plane.

13. The apparatus of claim 10 wherein:

said first and second apertures are disposed relatively remote from the symmetry plane, so that said $2\pi$ cycle of phase difference values consists essentially of phase difference values greater than 360 degrees.

14. The apparatus of claim 1 wherein:

each of the first and second apertures has a height, taken in said fringe movement direction, greater than about 0.75 times a projected fringe spacing of said projection of the interference fringes.

15. The apparatus of claim 1 wherein:

the first and second apertures are disposed within said beam plane.

16. The apparatus of claim 1 wherein:

said selected $2\pi$ cycle is an initial cycle incorporating phase difference values up to a maximum of 360 degrees.

17. A coherent energy detection device including:

an aperture for receiving coherent energy and transmitting the received energy therethrough, said;

a signal generating means for generating an electrical signal in response to a coherent energy input;

a coherent energy guiding means for receiving the coherent energy transmitted through the aperture and directing said coherent energy to the signal generating means; and Various desirable features of a non-linear response curve discussed above are met closely by an exponential function of the following form:

$$\overline{\Delta\phi}=\pi(1-e^{-d^*_p}) \quad (39)$$

This function eliminates the $2\pi$ ambiguity by confining the phase shift to $\pi$ for a single detector, i.e. the phase shift between two symmetric receivers would be restricted to $2\pi$.

The percent-of-the-reading sensitivity for the above response curve is obtained by substituting Equation (39) in Equation (33), so that $$S_{por}[\text{deg./\%}]=3.6d^*_p e^{-d^*_p}. \quad (40)$$

Although $S_{por}$ is not constant, it varies slowly and remains above 0.5 degrees per % in the range $0.2 \leqq d^*_p \leqq 3$. The largest value of $S_{por}$ is about 1.32% per % and occurs at $d^*_p=1$.

20. The device of claim 17 wherein:

the signal generating device includes an avalanche photo diode.

21. An apparatus for non-contact measurement of light scattering elements, including:

a beam generating means for generating two linearly propagating beams of coherent energy oriented at a predetermined beam angle relative to one another and intersecting one another to define a beam plane, said beams interfering with one another over a measuring region to form interference fringes extending across the measuring region in parallel fashion;

an alignment means operatively associated with the beam generating means for positioning the beams with respect to a composite flow so that light scattering elements within the composite flow move through the measuring region;

an energy detecting means for sensing the coherent energy scattered by each of the light scattering elements as it traverses the measuring region, said detecting means including first and second apertures at respective first and second locations spaced apart from the beam intersection zone, said energy detecting means generating respective first and second optical signals responsive to the energy received through the first and second apertures, respectively, and wherein the coherent energy received at each of the apertures includes a projection of said interference fringes traveling across the aperture in a fringe movement direction normal to a lengthwise extension of the projected fringes;

a data generating means for generating size information in response to receiving the first and second signals, said data generating means including a signal processing means for generating phase values representing temporal shifts between the first and second signals, and conversion means for generating said size information based on the phase values; and wherein each of the first and second apertures has a shape defined by opposite side boundaries extending generally in said fringe movement direction from a minimum height of the aperture to a maximum height of the aperture, and the side boundaries cooperate to define an aperture width that varies in said fringe movement direction according to a lognormal function.

$$\ln(x_{Ap}+x_{A0})-\frac{\sigma^2_{lgn}}{2}\ \Big\}-1;$$

$$A_{lgn}=(1+\Delta w)\exp\left[\ln(x_{Ap}+x_{A0})-\frac{\sigma^2_{lgn}}{2}\right]. \quad (44)$$

Equations (8)–(10) were solved numerically for the above aperture shape. This involves a solution of integrals whose integrands are oscillating and may have many oscillations within the range of integration. For solution of these integrals efficient numerical schemes, provided by Stamnes (Waves in Focal Regions, Part 2, IOP Publishing Limited, 1986) were used.

Simulations show that it is important to minimize $x_{Amin}$ in order to significantly extend the nominal size range beyond 1. However, there are practical limits on the minimum gap between two symmetrically located apertures. Using a practically achievable value for the minimum gap, an optimal lognormal aperture can be specified by the following combination of the shape parameters:

$$x_{Amin}=0.04,\ x_{A0}=0.1,\ x_{Ap}=0.16,\ \sigma_{lgn}=0.65$$

27. A process for measuring light scattering elements, including:

directing two linearly propagating beams of coherent energy into a composite flow including light scattering elements, such that the beams intersect one another over a beam intersection zone within the composite flow to form interference fringes extending across the beam intersection zone in parallel fashion;

detecting the coherent energy scattered by each of the light scattering elements as it traverses the beam intersection zone at first and second locations spaced apart from the beam intersection zone through first and second apertures, respectively, with the coherent energy received at each of the apertures including a projection of said interference fringes traveling across the aperture in a fringe movement direction normal to a lengthwise extension of the projected fringes;

selectively filtering the coherent energy received at each of the apertures to determine at each aperture a transmittance pattern in which a transmittance of the aperture is selectively varied in the fringe movement direction, thereby to select a non-linear phase/diameter function at least in a selected 2π cycle of phase difference values;

providing the selectively filtered coherent energy from the first and second apertures to respective first and second signal generating means, and using the signal generating means to generate respective first and second signals representative of phase;

generating phase difference values based on the first and second signals, to indicate a temporal shift between the first and second signals; and converting the phase difference values to scattering element diameters substantially according to the non-linear phase/diameter function over a diameter range corresponding to the selected 2π cycle of the phase difference values;

wherein the phase difference values are generated based on diameters of corresponding individual light scattering elements substantially according to the non-linear function.

* * * * *